United States Patent
Hemmer et al.

(10) Patent No.: US 12,121,302 B2
(45) Date of Patent: Oct. 22, 2024

(54) SYSTEM FOR PROVIDING REMOTE AND RAPID ACCESS TO SCANNED IMAGE DATA

(71) Applicant: CALIBER IMAGING & DIAGNOSTICS, INC., Rochester, NY (US)

(72) Inventors: Paul Michael Hemmer, Rochester, NY (US); Daniel L Gendreau, Webster, NY (US); Dower Chin, West Henrietta, NY (US); John Edward Werner, Fairport, NY (US)

(73) Assignee: CALIBER IMAGING & DIAGNOSTICS, INC., Rochester, NY (US)

( * ) Notice: Subject to any disclaimer, the term of this patent is extended or adjusted under 35 U.S.C. 154(b) by 363 days.

(21) Appl. No.: 17/359,285

(22) Filed: Jun. 25, 2021

(65) Prior Publication Data

US 2021/0401505 A1    Dec. 30, 2021

Related U.S. Application Data

(60) Provisional application No. 63/045,019, filed on Jun. 26, 2020.

(51) Int. Cl.
*A61B 34/00* (2016.01)
*A61B 34/10* (2016.01)
*G06T 7/00* (2017.01)

(52) U.S. Cl.
CPC .............. *A61B 34/10* (2016.02); *A61B 34/25* (2016.02); *G06T 7/0012* (2013.01); *A61B 2034/105* (2016.02); *A61B 2034/258* (2016.02)

(58) Field of Classification Search
CPC ......... A61B 34/00; A61B 34/10; A61B 34/25; A61B 2034/105; A61B 2034/258; G06T 7/0012; G06T 7/00
See application file for complete search history.

(56) References Cited

U.S. PATENT DOCUMENTS

| | | | |
|---|---|---|---|
| 4,860,112 A * | 8/1989 | Nichols | H04N 19/60 358/1.9 |
| 4,945,410 A | 7/1990 | Walling | |
| 5,005,126 A | 4/1991 | Haskin | |

(Continued)

FOREIGN PATENT DOCUMENTS

EP    2 862 327 B1    4/2015

OTHER PUBLICATIONS

Caliber Imaging & Diagnostics, Inc., VIVASCAN & VIVANET, http://www.caliberid.com/vivascan_Overview.html, printed Apr. 13, 2018.

(Continued)

*Primary Examiner* — Tuan H Nguyen
(74) *Attorney, Agent, or Firm* — Kenneth J. Lukacher; R. S. Rosenholm

(57) ABSTRACT

The invention provides a system, apparatus and method for providing remote and rapid access to image data. The invention can be employed during surgery to enable health care personnel, located away from a location where the surgery is being performed, to view and evaluate tissue excised from a patient during the surgery. Such health care personnel can provide feedback to the surgeon to enhance an outcome of the surgery.

21 Claims, 14 Drawing Sheets

(56) References Cited

U.S. PATENT DOCUMENTS

| | | |
|---|---|---|
| 5,235,510 A | 8/1993 | Yamada et al. |
| 5,297,034 A | 3/1994 | Weinstein |
| 5,374,965 A | 12/1994 | Kanno |
| 5,434,611 A | 7/1995 | Tamura |
| 5,441,047 A | 8/1995 | David et al. |
| 5,788,639 A | 8/1998 | Zavislan et al. |
| 5,793,969 A | 8/1998 | Kamentsky et al. |
| 5,836,877 A | 11/1998 | Zavislan |
| 6,014,451 A | 1/2000 | Berry et al. |
| 6,031,929 A | 2/2000 | Maitz et al. |
| 6,049,622 A | 4/2000 | Robb et al. |
| 6,101,265 A | 8/2000 | Bacus et al. |
| 6,208,374 B1 | 3/2001 | Clinch |
| 6,272,235 B1 | 8/2001 | Bacus et al. |
| 6,272,481 B1 | 8/2001 | Lawrence et al. |
| 6,500,122 B1 * | 12/2002 | Washburn ........... G01S 7/52073 600/443 |
| 6,606,413 B1 | 8/2003 | Zeinch |
| 6,608,628 B1 | 8/2003 | Ross et al. |
| 6,684,092 B2 | 1/2004 | Zavislan |
| 7,194,118 B1 | 3/2007 | Harris et al. |
| 7,394,592 B2 | 7/2008 | Fox et al. |
| 7,864,996 B2 | 1/2011 | Hemmer et al. |
| 8,463,741 B2 | 6/2013 | Ehlke et al. |
| 9,055,867 B2 | 6/2015 | Fox et al. |
| 9,230,153 B2 | 1/2016 | Casas |
| 9,495,577 B2 | 11/2016 | Casas |
| 9,709,791 B2 | 7/2017 | Hemmer |
| 9,871,960 B2 | 1/2018 | Casas |
| 9,883,093 B2 | 1/2018 | Casas |
| 10,459,211 B2 | 10/2019 | Hadley et al. |
| 10,466,460 B2 | 11/2019 | Gareau |
| 10,908,406 B2 | 2/2021 | Hadley et al. |
| 2002/0019751 A1 | 2/2002 | Rothschild et al. |
| 2004/0210582 A1 | 10/2004 | Chatterjee et al. |
| 2005/0060202 A1 | 3/2005 | Taylor et al. |
| 2010/0235323 A1 | 9/2010 | Zhang et al. |
| 2011/0197241 A1 | 8/2011 | Creamer et al. |
| 2018/0032677 A1 | 2/2018 | Adriaensens |
| 2019/0265456 A1 | 8/2019 | Fox et al. |

OTHER PUBLICATIONS

Rajadhyaksha et al., In Vivo Confocal Scanning Laser Microscopy of Human Skin: Melanin Provides Strong Contrast, Journal of Investigative Dermatology, vol. 104, No. 6, pp. 946-952, Jun. 1995.
Rajadhyaksha et al., Confocal Laser Microscope Images Tissue in vivo, Laser Focus World, pp. 119-127, Feb. 1997.
VivaScope® 2500 Multilaser, MAVIG GmbH, 2010.
Vivascope®, MAVIG GmbH, 2011.
VivaScope® 1500/3000, MAVIG GmbH, 2018.
VivaScope® 2500M-G4, MAVIG GmbH, 2019.
Extended European Search Report, European Patent Application No. 218279915.6, Mailed May 14, 2024.

* cited by examiner

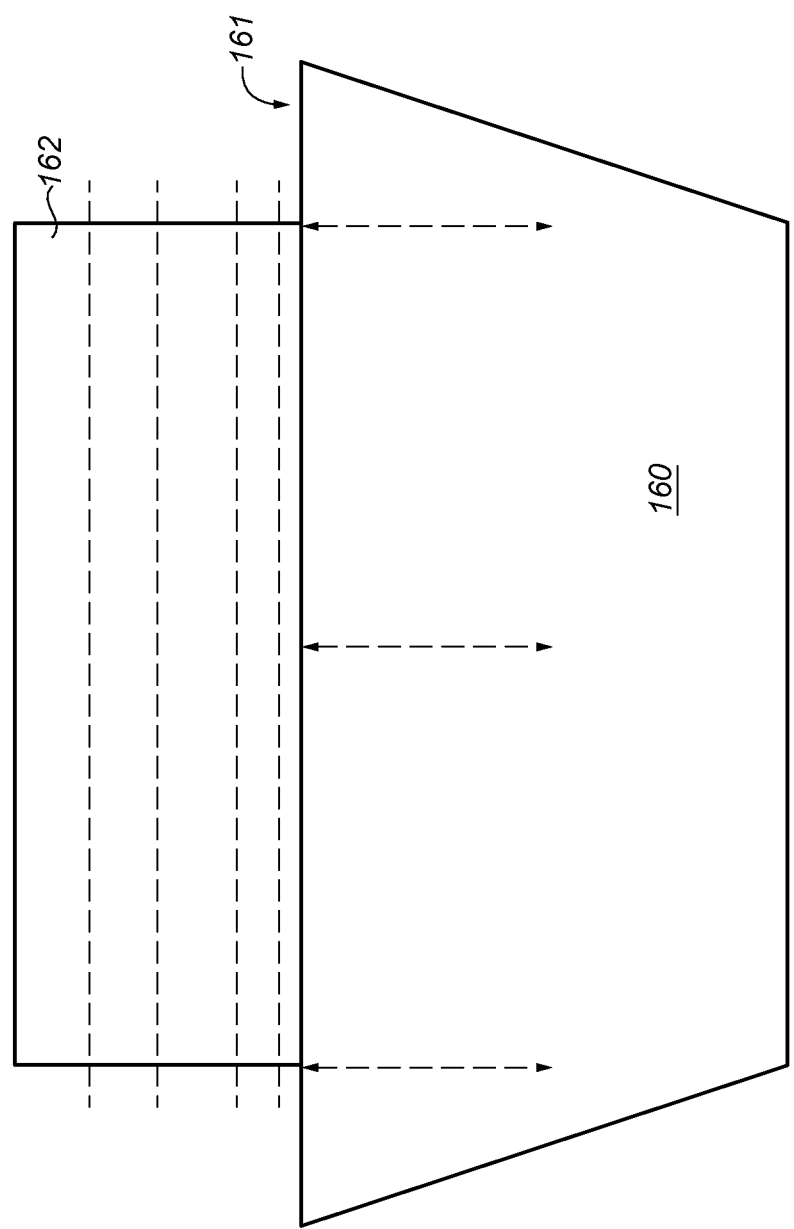

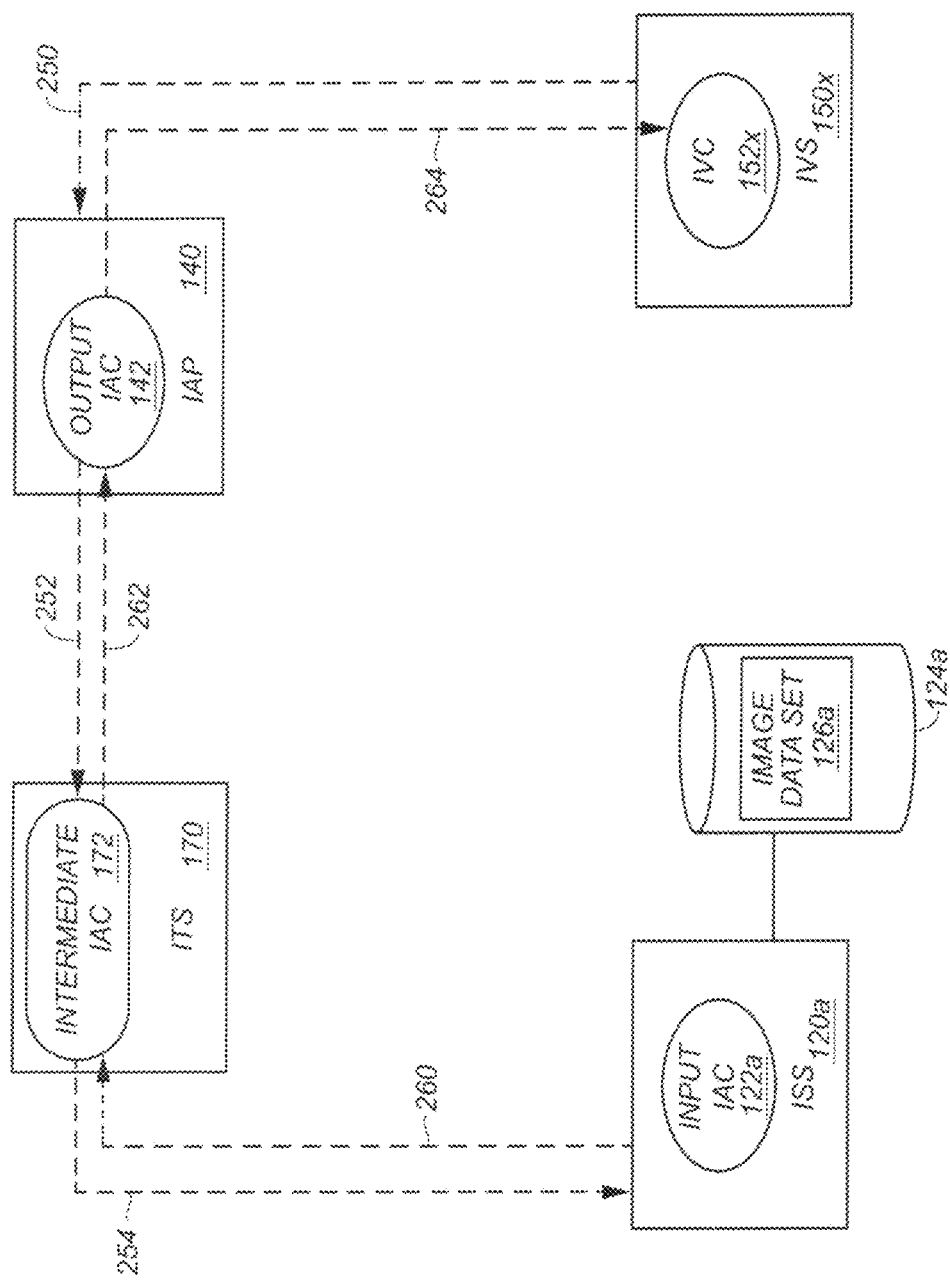

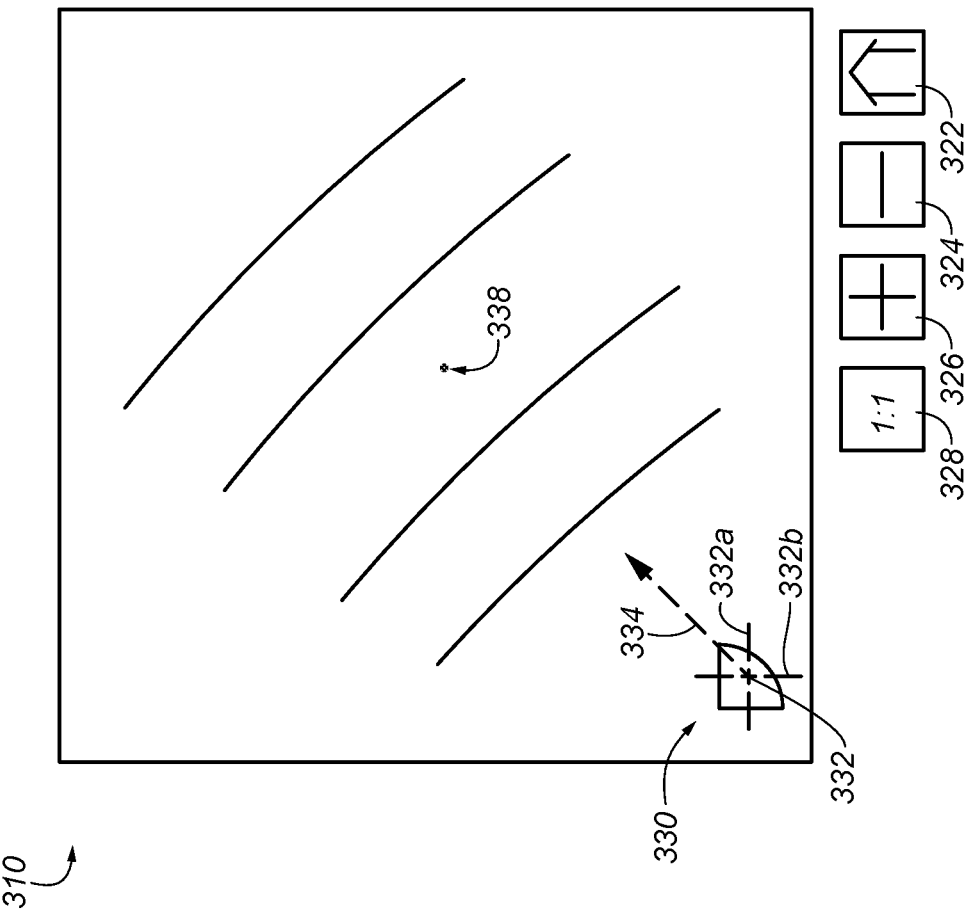
FIG. 3B
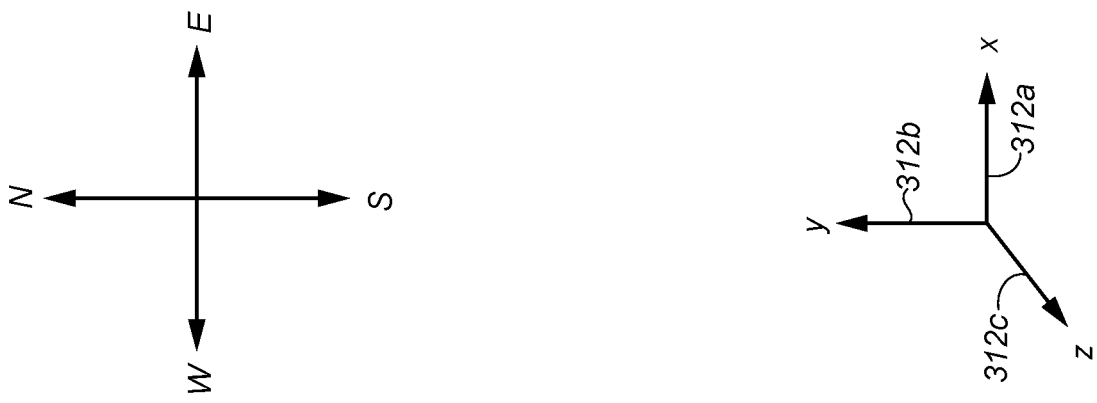

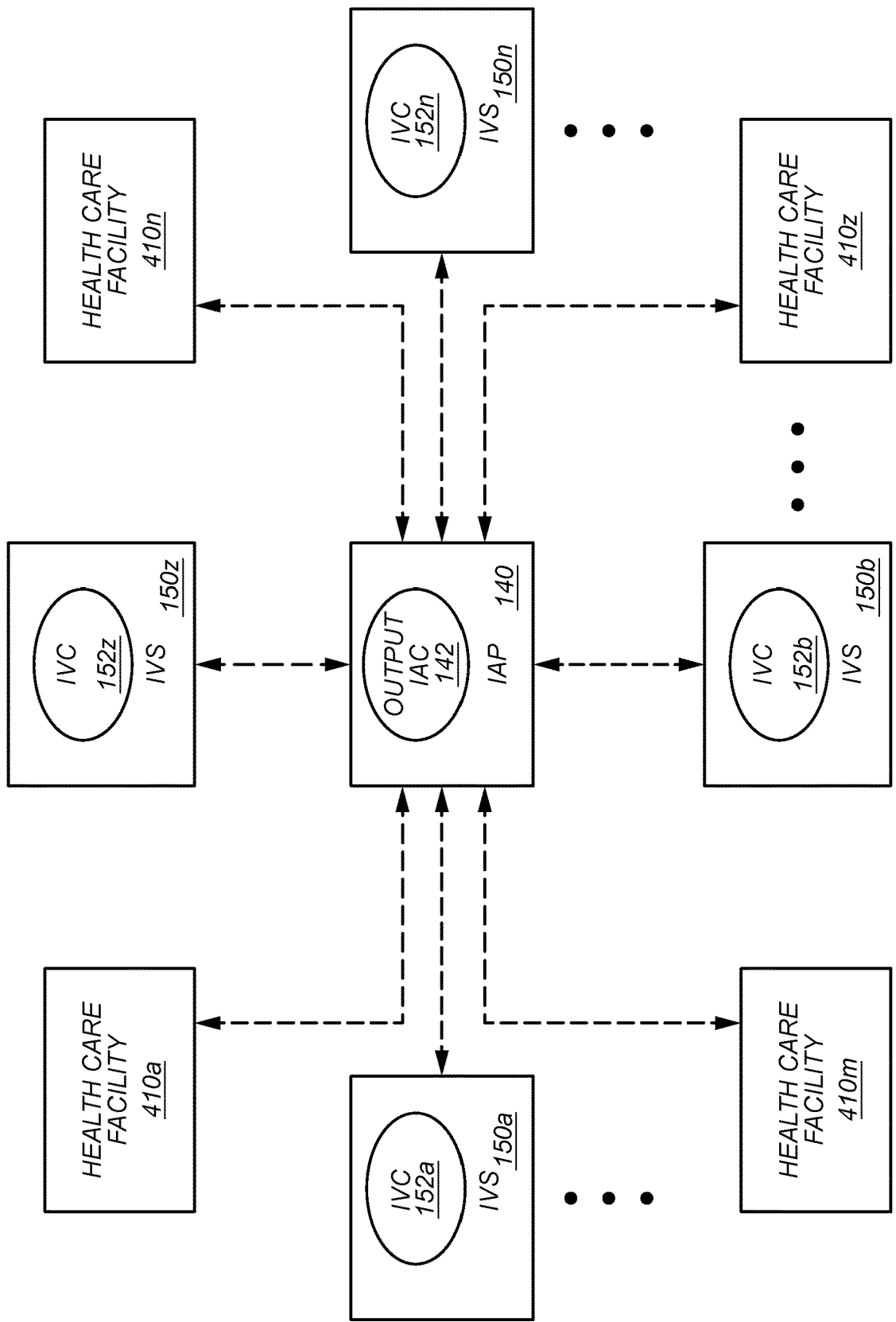

SYSTEM FOR PROVIDING REMOTE AND RAPID ACCESS TO SCANNED IMAGE DATA

CROSS REFERENCE TO RELATED PATENT APPLICATION(S)

This document is a United States non-provisional utility patent application that claims priority and benefit to U.S. (utility) provisional patent application having Ser. No. (63/045,019), (Confirmation No. 4651), that was filed on Jun. 26, 2020, and that is entitled "SYSTEM FOR PROVIDING REMOTE AND RAPID ACCESS TO SCANNED IMAGE DATA", and which is incorporated herein by reference in its entirety.

PATENT APPLICATION(S) INCLUDING RELATED SUBJECT MATTER

This document includes subject matter generally related to that of U.S. Pat. No. 9,055,867 to Fox et al., that was issued on Jun. 16, 2015 and entitled "CONFOCAL SCANNING MICROSCOPE HAVING OPTICAL AND SCANNING SYSTEMS WHICH PROVIDE A HANDHELD IMAGING HEAD".

This document includes subject matter that is also generally related to that of U.S. Pat. No. 10,908,406 to Hadley et al., that was issued on Feb. 2, 2021 and entitled "RESONANT SCANNER INTEROPERATION WITH MOVABLE STAGE".

All of the above aforementioned documents, including patents, patent publications, patent applications and technical papers are incorporated herein by reference in their entirety.

BACKGROUND OF THE INVENTION

Performing medical surgery upon a patient typically involves cutting and/or removal of tissue from the body of the patient. Tissue removed from the body of the patient can be evaluated visually and/or can be evaluated via one or more devices that can reveal characteristics of the tissue that cannot necessarily be seen from the human eye. Such devices employed for evaluation, include for example, a confocal laser scanning microscope, which is designed to produce a representation of one or more characteristics of the removed tissue. Such a representation can be encoded and stored as digitally encoded data.

The discussion above is merely provided for general background information and is not intended to be used as an aid in determining the scope of the claimed subject matter.

BRIEF DESCRIPTION OF THE INVENTION

The invention provides a system, apparatus and method for providing remote and rapid access to image data of ex-vivo tissue excised from a patient during surgery. The invention can be employed during performance of the surgery to enable other remotely located health care personnel, to view and promptly evaluate tissue excised from the patient during the surgery. Such health care personnel can provide rapid and timely feedback to the surgeon during performance of the surgery, in order to expedite and enhance the outcome of the surgery.

This brief description of the invention is intended only to provide a brief overview of subject matter disclosed herein according to one or more illustrative embodiments, and does not serve as a guide to interpreting the claims or to define or limit the scope of the invention, which is defined only by the appended claims.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention can encompass other equally effective embodiments.

The drawings are not necessarily to scale. The emphasis of the drawings is generally being placed upon illustrating the features of certain embodiments of the invention. In the drawings, like numerals are used to indicate like parts throughout the various views. Differences between like parts may cause those parts to be indicated with different numerals. Unlike parts are indicated with different numerals. Thus, for further understanding of the invention, reference can be made to the following detailed description, read in connection with the drawings in which:

FIG. 2B illustrates a simplified representation of an embodiment of the image scanner of FIG. 2A.

FIG. 2F illustrates operation of the set of image access components of FIG. 2E.

FIG. 3B illustrates communication of a coordinate directive from a user of the image stream viewing station.

FIG. 4 illustrates an expanded overview of communication of image data involving multiple health care facilities.

DETAILED DESCRIPTION OF THE INVENTION

Figure 1:
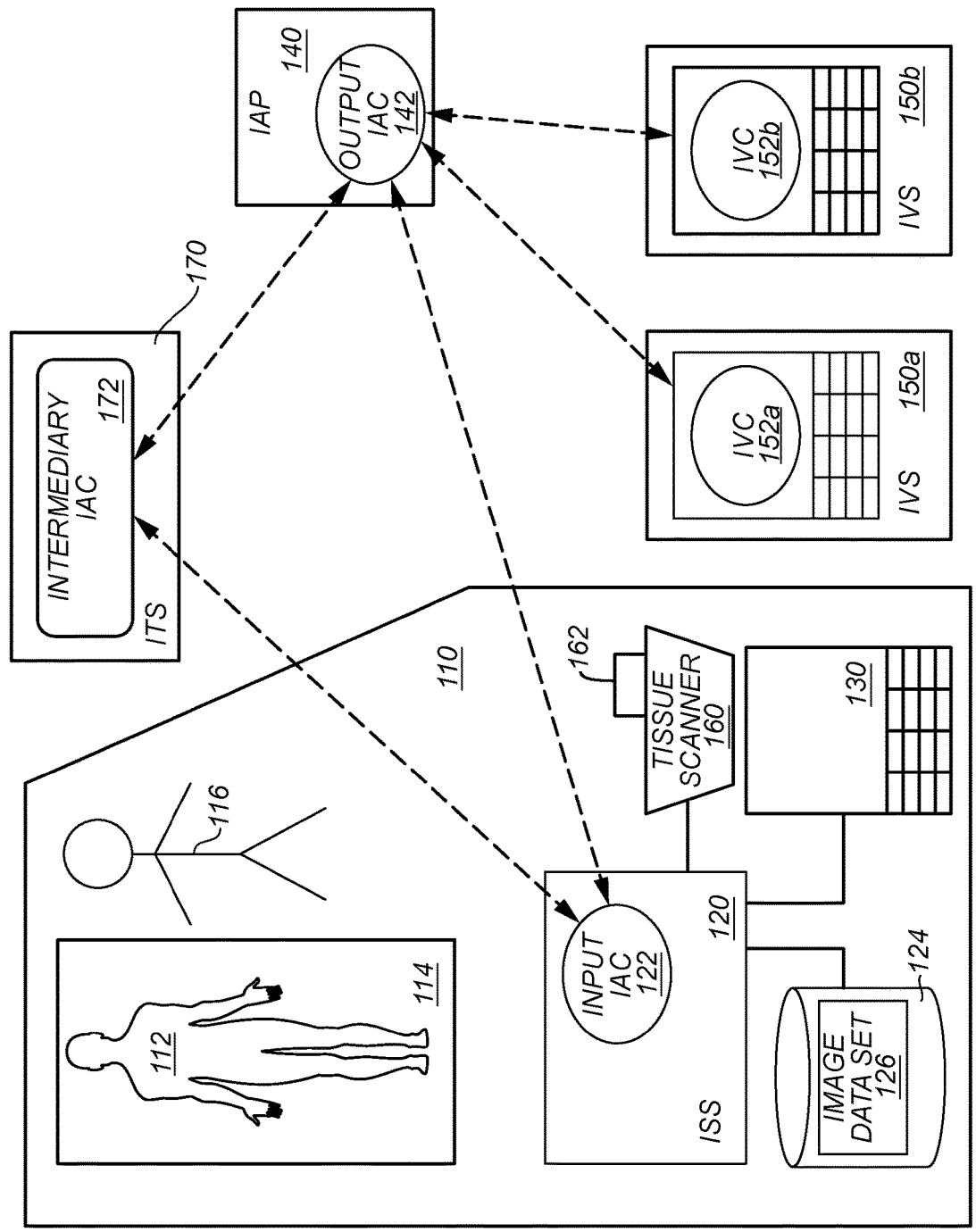
FIG. 1 illustrates a simplified overview of an embodiment of a system for communication of image data that is scanned from tissue excised from a patient during surgery.

FIG. 1 illustrates a simplified overview of an embodiment of a system for communication of image data that is scanned from tissue 162 excised from a patient during surgery. This illustration shows a top-down perspective of a first health care facility 110 where surgery is being performed by a surgeon 116 upon a patient 112. The patient 112 is shown as lying upon an operating table 114. The surgeon 116 is acting as a physician and as a first health care specialist within the first health care facility.

During the surgery, an ex-vivo sample of tissue 162 is excised (cut) from the body of the patient 112 by the surgeon 116. The ex-vivo tissue sample 162 is transported to an image scanning station (ISS) 120 that is located within the first health care facility 110, to be optically scanned via a confocal scanner 160 in order to generate a large set of electronically encoded and stored data, which in this circumstance is digitally encoded image data, and which is referred to herein as image data 126 or as an image data set 126.

Another second health care specialist, being a physician licensed as a pathologist, is scheduled to evaluate the excised ex-vivo tissue sample 162 for the presence or absence of an unhealthy condition. The second health care specialist being located in a second health care facility that is located remote from and many miles from the first health care facility, during performance of the surgery. Such an unhealthy condition could be indicated by a presence of disease within the excised tissue 162, for example, such as by the presence of a cancerous lesion, for example. The performance of the surgery is suspended until the first health care specialist, being the surgeon 116 receives a satisfactory evaluation of the excised tissue sample 162 from the second health care specialist, being the pathologist.

Upon completion of scanning of the ex-vivo tissue sample 162, the resulting scanned image data 126 undergoes a processing stage so that the image data 126 can be more effectively viewed from a remote location by various persons having permission to view such data, including such as the pathologist. The ISS 120 includes an Input image access component (Input IAC) 122 that is configured to communicate the existence of and the availability of the processed image data, stored within an image data set 126, for access or viewing by one or more persons, via image viewing stations (IVS) 150a-150b. Processed image data is also referred to herein as image data or data.

When the processed image data becomes available for access or viewing, an event which is also referred to herein as processed image data becoming available, the processed image data can be accessed for applications other than for viewing. For example, the processed image data can be stored within temporary and/or permanent storage that is located away (remote) from the location of surgery, in order for (a copy of) such data to be made quickly available for (parallel) access from locations away (remote) from the location of surgery, and without requiring any further involvement of the image scanning station (ISS), when providing such available and parallel access.

Or, such processed image data can be further processed via hardware and/or software from a location that is located away (remote) from the location of surgery. Such further processing can include, for example, employment of artificial intelligence for the purpose of evaluating a likelihood of a presence of disease, or some other type of anomaly within the tissue from which the image data was scanned.

Upon completion of the processing of the image data, the Input IAC 122 communicates (causing notification of) the existence and availability of the processed image data, to persons having permission to view such data. The image viewing stations (IVS) 150a-150b are configured to provide access and viewing of the image data 126 from a remote location by each of such persons, via the Internet, or via another type of network.

Figure 2A:
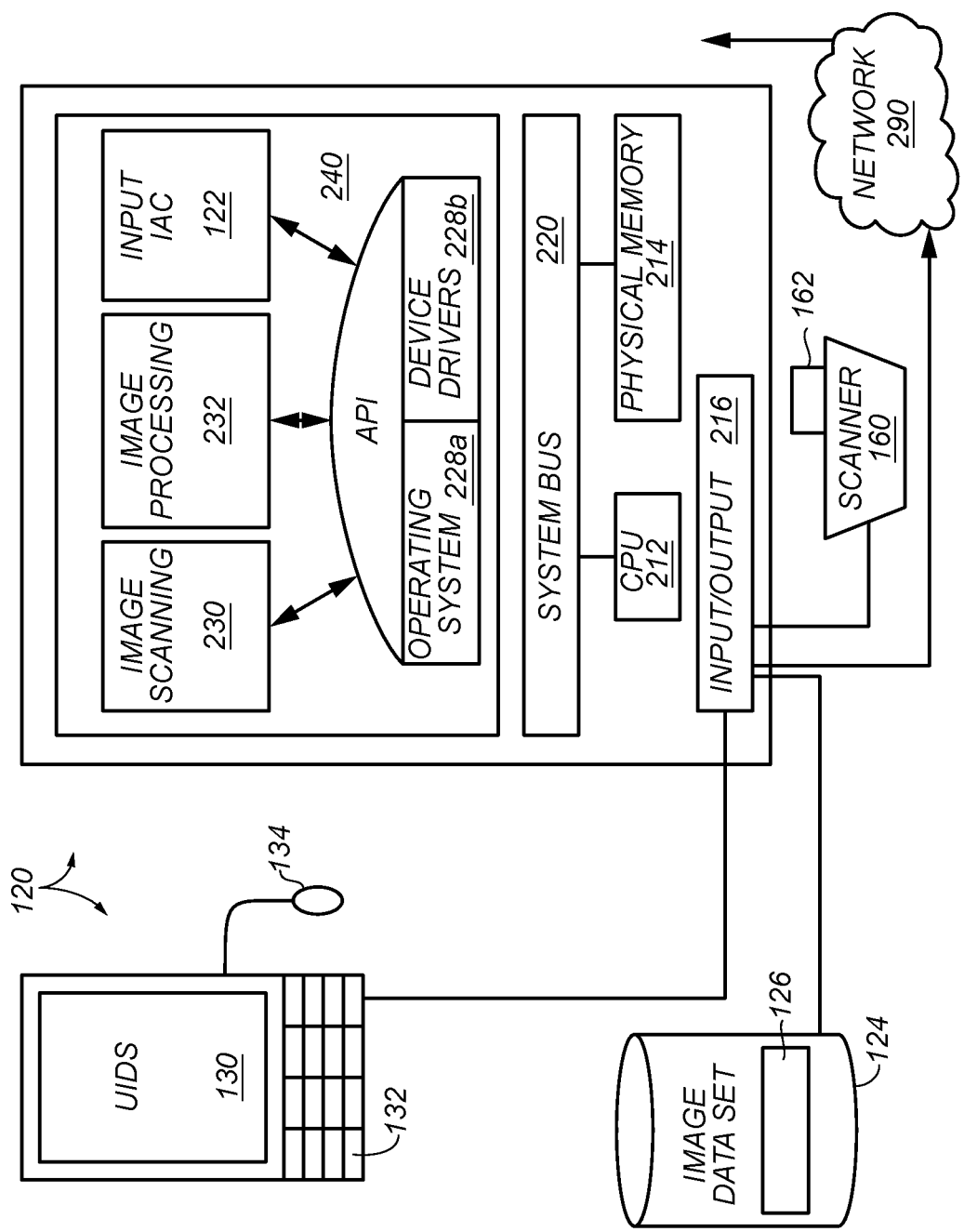
FIG. 2A illustrates a simplified representation of an embodiment of the image scanning station (ISS).
Figure 2C:
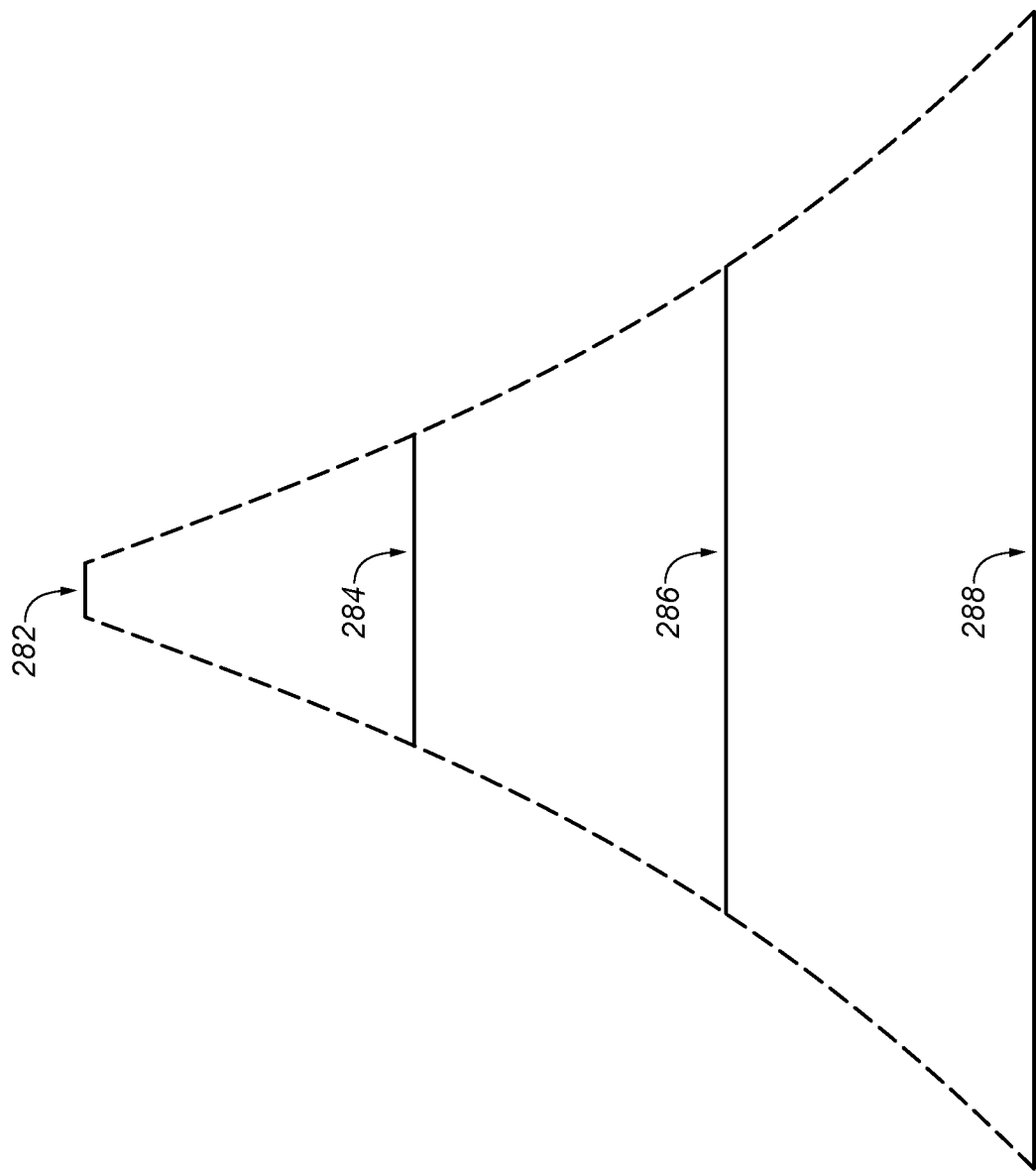
FIG. 2C illustrates various resolutions of image data that can be employed for viewing the exposed surface of excised tissue.
Figure 2D:
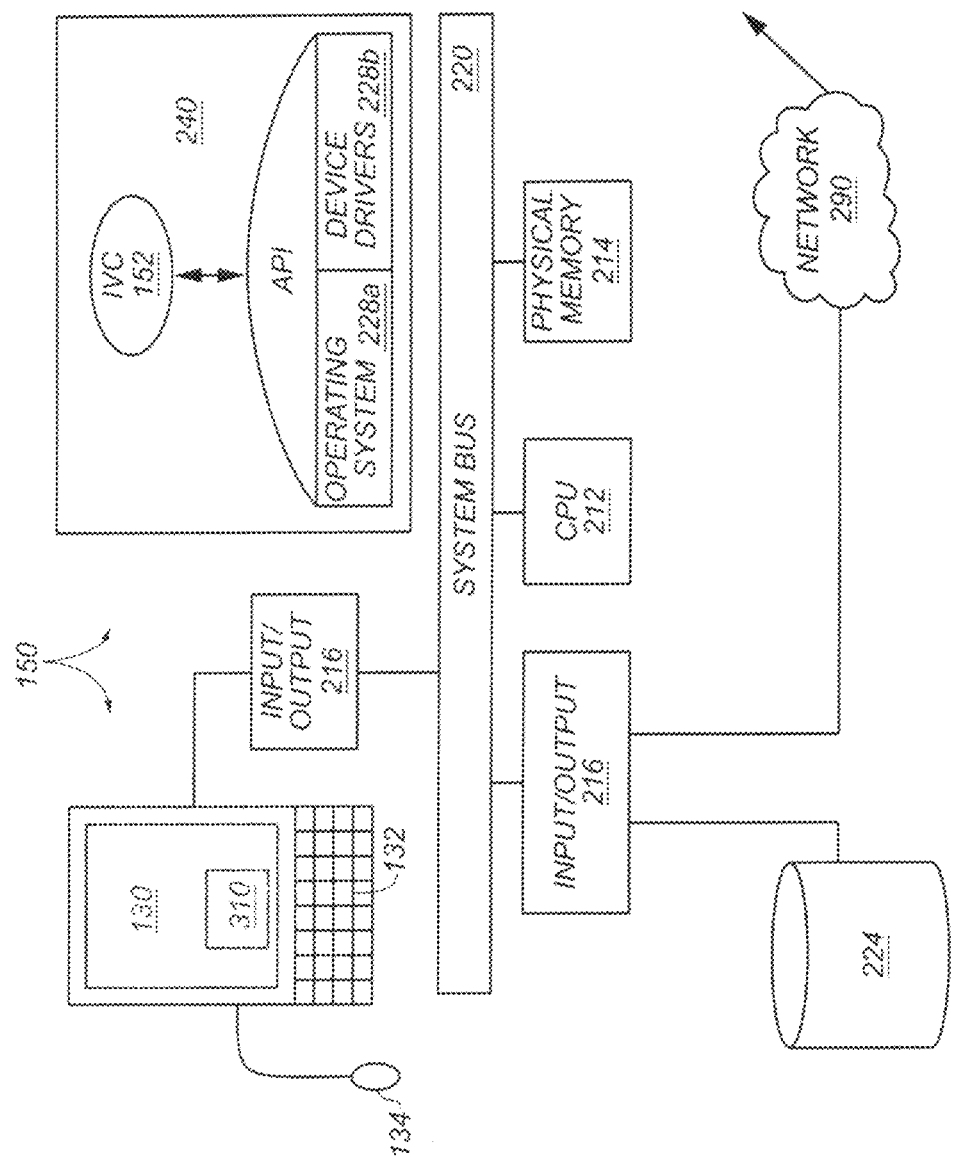
FIG. 2D illustrates a simplified representation of an embodiment of the image viewing station (IVS).
Figure 2E:
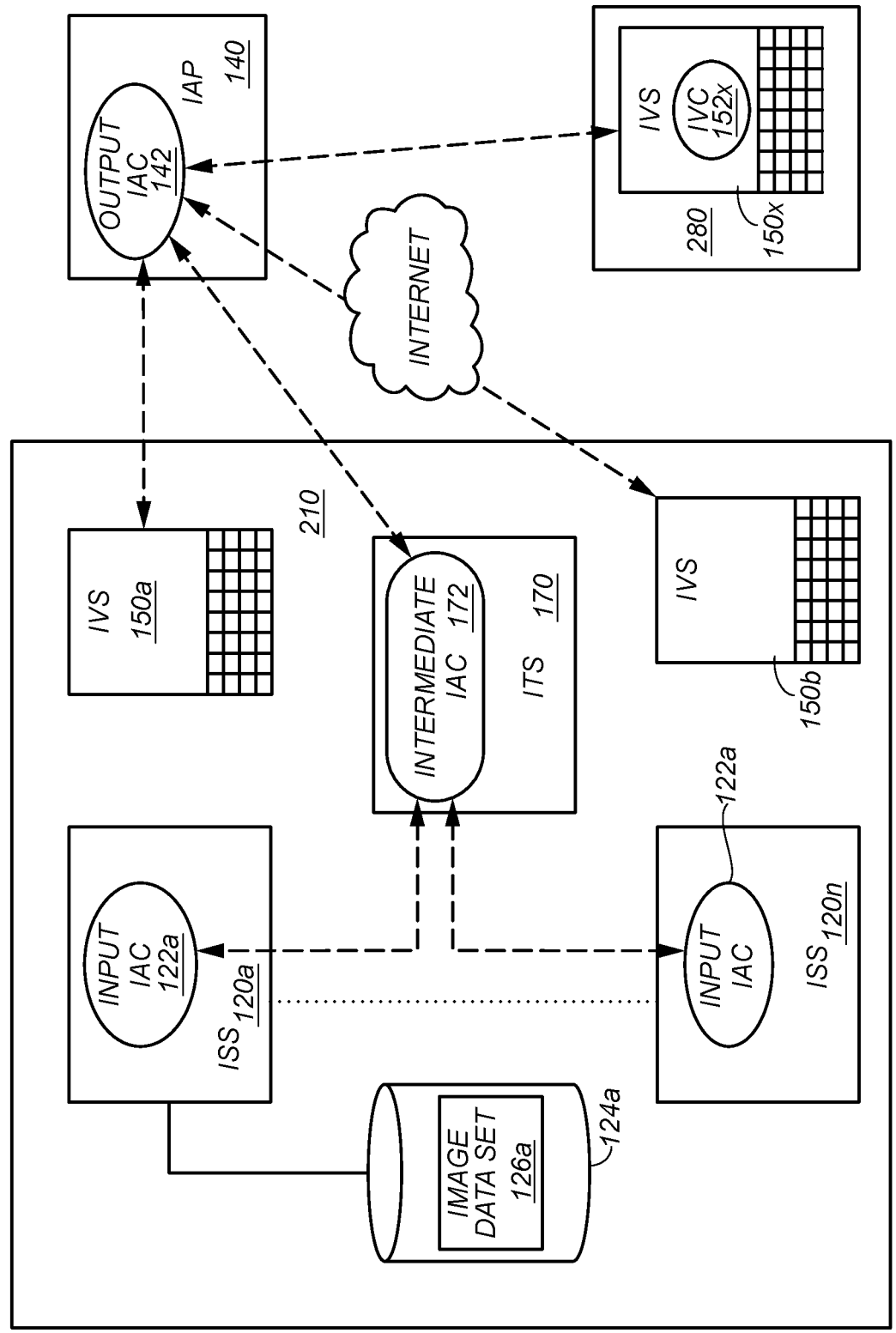
FIG. 2E illustrates a simplified representation of an embodiment of a system including a tree type of hierarchy of a set of image access components.

As illustrated in FIG. 2E, the Input IAC 122 interoperates with other members of a set of image access components (IACs) to communicate the existence and availability of the image data set 126 for viewing. The set of IACs includes at least one Input IAC 122, one Output IAC, and optionally, one or more Intermediate IAC(s). An Intermediate IAC operates as an intermediary between two other IACs.

The IACs interoperate with each other to communicate image data within the image data set 126 to a viewer of the image data via an image viewing station 150 on demand. An image viewing station (IVS) 150 is employed to enable viewing of the image data by the pathologist (viewer) from a remote location.

The IVS 150 interoperates with the Output IAC 142 that is executing upon (hosted by) an Internet accessible web site, referred to herein as an image access portal (IAP) 140. The Output IAC 142 locates and communicates image data for the pathologist to view remotely and rapidly, on demand and in response to viewing directives communicated from the pathologist, being a user of the IVS 150, to the IVS 150. A pathway between the Output IAC 142 and an image data set 126 to be accessed for viewing, including another image access components (IACs) that facilitate such access between the Output IAC 142 and the image data set 126, is referred to herein as an image access pathway of communication or as an access pathway of communication.

The system enables multiple image viewing stations (IVSs) 150a-150b to view the image data set 126 from a plurality of remote locations each during a period of time can overlap concurrently between multiple IVSs 150a-150b or occur separately over time. Also, one viewing station (IVS) is configured to view multiple image data sets at one time.

In a circumstance where the surgeon 116 receives an unsatisfactory evaluation of the tissue 162 sample from the pathologist, the surgeon 116 may be motivated and/or required to excise a second tissue sample from the patient 112, for re-scanning in order to generate a second set of image data for the second tissue sample in order to enable a second evaluation for the second tissue sample from the pathologist. Once evaluation of the excised tissue is satisfactory, the surgeon is typically free to continue on with and complete the surgery.

FIG. 2A illustrates a simplified representation of an embodiment of the image scanning station (ISS) 120. The ISS 120 is designed for optically scanning ex-vivo tissue that is excised during surgery. In this embodiment, the ISS 120 is preferably a desktop computer. As such, a desktop computer includes at least one central processing unit (CPU) 212, a system bus 220, physical memory 214, virtual memory 240 and input/output hardware 216, that is designed to provide electronic interface(s) to one or more peripheral devices, including an electronic interface to a network 290. The ISS 120, being a desktop computer, also includes user interface hardware, including a user interface display screen (UIDS) 130, a keyboard 132, a mouse (screen pointer) device 134. The user interface hardware provides a user interface to enable a user of the ISS 120 to interact with and operate the ISS 120.

The image scanning station 120 also includes peripheral devices, including an attached confocal (optical) scanner device 160 and a data storage device 124, which is also referred to herein as a mass storage device 124, or as a storage device 124. In this embodiment, the scanner 160 includes optics that enable optical scanning of the ex-vivo tissue 162 at a resolution of one-quarter micron pixels or smaller. The data storage device 124 is a one terabyte solid state disc having a read/write data rate equal to 400 megabytes per second. Optionally and in other embodiments, the ISS 120 could also include other hardware and software that is not necessary for perform optical scanning of excised tissue 162.

As for software, in this embodiment, the ISS 120 is installed with Microsoft Windows operating system (OS) software 228a, and preferably the Windows 10 operating system software 222. The operating system (OS) including device drivers 228b to interface with peripheral devices that are attached to the ISS 120. The ISS 120 is installed with software application programs, including an image scanning component (ISC) 230, an image processing component (232) and an Input Image Access Component (Input IAC) 122. Optionally, the ISS 120 includes at least one web browser program, such as for example, a Google Chrome browser program.

FIG. 2B illustrates a simplified representation of an embodiment of the image scanner 160 of FIG. 2A. In this embodiment, the scanner 160 is a confocal image scanner 160. Operation of the image scanner 160 will be described in association with a first use scenario.

In the first use scenario, a sample of ex-vivo tissue 162 is excised (cut) from surgery patient 112 during surgery. The excised ex-vivo tissue 162 is also referred to herein as the tissue 162 or tissue 162. Prior to completion of the surgery, the tissue 162 is transported to the scanner 160. In this scenario, the scanner 160 is a confocal (optical) scanner 160, and is also referred to herein as the scanner 160. The scanner 160 is typically located within walking distance from the location where the surgery is taking place.

Typically, the surgeon 116 cuts tissue 162 from within the patient at a particular location to expose a surface of the tissue for inspection. The inspection searches for a presence of an abnormality within the tissue 162 that could be indicative an unhealthy condition, such as a presence of some type of disease, including a presence of some type of cancer. The inspection is typically performed by a health care specialist, such as by a pathologist and/or someone who has a special skill towards identifying such types of abnormalities. Such abnormalities being evidence of a presence of a particular un-healthy condition that could be visible along the exposed surface of the tissue.

In a circumstance where an unhealthy condition is identified along the surface of the tissue 162, the surgeon 116 is typically required to continue to perform surgery and to excise more tissue from the patient in search of tissue having a healthy surface.

When excised tissue is determined to have a healthy surface, this excised tissue is also referred to as having a healthy margin of tissue, or as having a healthy margin. If such a healthy margin of tissue is obtained by the surgeon, this event is typically an indication that a sufficient amount of unhealthy tissue that is the focus of the surgery, has been removed from the patient 112, in order to permit the surgeon 116 to continue on with completion of the surgery.

Alternatively, in a circumstance where the surface of the tissue appears to be healthy, the surgeon 116 is typically free to continue on with completing the surgery without necessarily being required to cut additional samples of tissue from the patient.

In this embodiment, the scanner includes an upward facing and transparent substrate, also referred to herein as a platen 161. The tissue 162 includes one or more surfaces that are exposed from the cutting of tissue from within the patient by the surgeon 116. One such exposed surface is selected for image scanning, and is placed (facing downwards as shown) upon an upper surface of the platen 161 and facing towards the body (chassis) of the scanner 160.

During operation, the scanner 160 is designed to project particular wavelengths of light in an upward direction from the body of the scanner 160 and through the platen 161 and towards the exposed surface of the tissue 162. The light projected upward causes reflection and/or fluorescence of light from the exposed surface of the tissue 162. Reflected and/or fluoresced light is generally directed back towards the body of the scanner 160. The reflected and/or fluoresced light is detected and stored as image data within the scanner 160.

The scanner 160 is designed to scan the tissue along a two dimensional plane, also referred to herein as a scanning plane. The location of such a scanning plane can be adjusted. As shown, the tissue 162 can be scanned along a scanning plane that is defined along the exposed surface of the tissue 162, or the tissue 162 can be scanned along a scanning plane that is located a small distance into the body of the tissue 162. This small distance is also referred to herein as a scanning depth. The scanning depth can be set to a physical distance (depth) of one micron through the surface and into the body of the tissue 162, or set to a physical distance (depth) equal to a multiple of 5 micron increments into the body of the tissue 162 from the surface of the tissue 162, for example.

The image data is stored in units of data, which are referred to herein as image data pixels or as data pixels. Each data pixel represents a small portion of an image. Each small portion of the image is detected by light reflecting and/or fluorescing from the tissue 162. In this embodiment, each data pixel requires two bytes of storage per channel. These two bytes encode a grayscale intensity representing that small portion of the image.

Each data pixel can be represented in a variety of different ways. These different ways are referred to herein as channels. By default, no dye is applied to the tissue 162 and optical scanning of the tissue 162 gathers projected light that is reflected (not fluoresced) from the tissue 162.

Alternatively, one or more fluorescent dye(s) can be applied to the tissue 162 prior to scanning the tissue 162. In this circumstance, while scanning the tissue 162, particular (discrete) wavelengths of light are directed at the tissue 162 to cause the tissue 162 to fluoresce (optically shine) in response to contact with these discrete wavelengths of light. This optical shine is fluoresced light that is within a range of wavelengths (color). Such an optical shine provides information that can be employed to colorize a representation of the tissue.

Each perspective from which the tissue 162 is represented by image data is referred to herein as a channel. If a portion of tissue 162 undergoes a first optical scanning without a dye, the image data obtained from this first type of optical scanning, is referred to as one channel or as a first channel of image data. This first channel of image data is of a type that is also referred to herein as a channel of reflective image data, or referred to as a reflective channel of image data, for the scanning of that tissue 162.

If alternatively, that tissue is dyed, and fluoresced and undergoes an optical scanning while being fluoresced, then the image data gathered from this alternative scanning of the tissue is referred to as a channel of fluoresced image data, or referred to as one fluoresced channel of image data for that tissue.

If that same tissue undergoes a first reflective optical scanning and the second fluoresced optical scanning, then the combined image data for that portion of tissue is referred to herein as having two channels of image data for that portion of tissue. The first channel being reflective channel and the second channel being fluoresced channel of image data. Preferably, the same two channels of image data are obtained while the first reflective optical scanning and the second fluoresced scanning are performed simultaneously (at the same time). In the use scenario to be described, the exposed surface of tissue is square in shape and is 25 millimeters in width and 25 millimeters in height, and has a total area size equal to (25 millimeters×25 millimeters=625 square millimeters).

In this use scenario, the exposed surface of tissue is optically scanned. Optionally, the exposed surface can be scanned in a matrix type of pattern, where each element of the matrix, being an intersection of a row and a column within the matrix, represents a portion of the area of the exposed surface of tissue. This type of scanning is also referred to herein as step mapping or step scanning, or as block (mosaic) mapping or block scanning. This portion (block) within the matrix is approximately square in shape and is referred to herein as a frame, or scanning field of view.

A frame is also referred to herein as a field of view (FOV), because it can be later displayed and viewed after being scanned. With this type of scanning, the exposed surface is optically scanned in such block portions that are each referred to as being one frame at a time, until all of the frames along the exposed surface of tissue are scanned. Alternatively, another type of scanning is referred to herein as strip mapping or strip scanning, where the exposed surface is optically scanned at one time over portions that are larger (larger portions) than those scanned via of block scanning, and where each larger portion is typically longer in one dimension, and typically having an overall size that is larger in total area than one scanned block.

In this embodiment, the scanner 160 is configurable to scan within a range of scanning resolutions. The highest scanning resolution within this range is referred to herein as a full scanning resolution. When employing block scanning, at a highest (full) scanning resolution, the exposed surface of tissue is divided into a matrix including at least 100 rows and at least 100 columns, defining a matrix of at least 10,000 scanning fields of view, including at least 10,000 elements within the matrix of rows and columns. The language "at least" is employed to account for scanning frame overlap, which requires more frames to be scanned, than frames to be displayed and viewed, and which is described further below. Within each frame (scanning field of view) there is another matrix, being a matrix of image data pixels. This matrix of image data pixels within each frame includes at least 1024 rows and 1024 columns of image data pixels.

Within this embodiment of the invention and invention use scenario, the exposed surface of the tissue 162 is optically scanned at a full (highest) scanning resolution while employing block scanning. At full scanning resolution, each frame includes a matrix of data pixels. Each data pixel represents an approximately square shaped area of tissue that measures approximately 0.24 microns in width and approximately 0.24 microns in height. These data pixels are nominally referred to herein as one quarter micron data pixels, as an approximate linear measure of their size. Each frame represents an approximately square shaped area of tissue that measures approximately 240 microns in width and approximately 240 microns in height.

At the full scanning resolution, the 25 millimeter square exposed surface area of the tissue requires scanning frames that are arranged into at least 100 rows and 100 columns of scanning, that each slightly overlap each other. This slight overlap of each scanning frame, referred to as frame overlap, better enables software, referred to as image stitching software, to join adjacent scanning frames together to form a uniform (stitched) image data representation of the image of the entire exposed surface of tissue.

As a result, such overlap requires more than (100 rows× 100 columns=10,000) separate scanning frames to generate 10,000 stitched together displayable and viewable frames, which are each referred to as a display field of view or viewing field of view. Each scanned frame (field of view) includes 1024 rows×1024 columns of data pixels=1,048, 576, (more than one million) data pixels. Requiring two bytes of storage for each data pixel, each scanned frame (field of view) requires slightly more than 2 million bytes (2 megabytes) of image data, per channel of scanned image data.

As a result, an amount of image data that is required to scan this surface area of approximately one square inch (25 millimeters×25 millimeters=625 square millimeters) in are size would require more than approximately 20 billion bytes, being 20 gigabytes of image data per channel.

In many circumstances, a potential viewer (user) of the image data, such as a health care specialist that is expected to evaluate the excised tissue, might not be located within a convenient walking distance to the surgery. Instead, this specialist could be located on another floor of the same building, or located in another building within a campus of the health care facility, or located at another health care facility and/or located miles away from where the surgery is being performed.

Software designed to input, process and output the image data for viewing by a viewer (user) of the image data, normally requires a high data rate access to the image data, or else, too much time will be spent by the software and by a user of the software, waiting for the software to input such a large amount of image data (more than 20 gigabytes per channel) that is desired to be viewed by the user.

Typically, having high data rate access to image data requires that an entirety of the image data be accessible by a computer having a directly attached data storage device. A storage device is referred to herein as being directly attached to a computer is when it is physically attached and located proximate to the computer, and without an intervening network.

As shown in FIG. 2A, input/output hardware 216 is situated between the system bus 220 of the computer and the storage device 124. As is shown in FIG. 2A, only the input/output hardware 216, which is local to and physically attached to the system bus 220 of the computer of the ISS 120, is situated between the system bus 220 and the storage device 124.

Typically, a directly attached storage device provides access to data that is at or near the maximum speed of the storage device, and typically at a rate of 50 megabytes or more per second. However, if for example, a network or some other type of communications channel is situated between the system bus 220 of the computer and the storage device 124, the network can span a far distance away from the system bus 220 of the computer of the ISS 120, and as a result, the data transfer rate to/from the storage device typically drops far below that of 50 megabytes per second, and as a result, the storage device 124 is not considered herein to be directly attached to the computer of the ISS 120.

For example, a local area network can span across a distance of one half of a mile and deliver data at about 10 megabytes per second. A distance in excess of one half of a mile is referred to herein as a wide area network distance.

Potentially, each viewer of the image data may focus their attention on viewing different portions of the image data, and/or viewing portions of image data in a different sequence over time, depending upon what characteristics are being searched for and inspected by whom, within such a large amount of image data. Ideally, the entirety of the image data should be available to be accessed and viewed interactively and flexibly by the user (viewer) in a time efficient manner.

One option to achieve the above stated goal would be to upload the entirety of the image data to wide area network, such as for example, an internet accessible web site. The web site would be provided a high data rate access to the image data. Having high data rate access to the image data, the internet accessible web site could then be accessed by users (viewers) from a variety of geographical locations. However, there are some problems with this approach.

A typical (standard internet) uploading speed from a work station, such as an image scanning station, to the Internet is about 2-3 Megabytes per second. At data rate equal to 2.5 megabytes per second, if one channel image scanning were performed for this 625 square millimeter tissue specimen, then uploading the one channel image data would require about 8000 seconds, which would be equal to about 133 minutes, being more than 2 hours, prior to a health care specialist being able to view the image data. Alternatively, if two channels of image scanning were performed for this tissue specimen, then uploading the two channels image data to the Internet would require more than 4 hours, prior to viewing the image data.

During surgery, it is not practical to suspend surgery and wait for a period of one or more hours for a health care specialist, such as a pathologist to inspect and evaluate the exposed surface of the excised tissue. While waiting for an evaluation of the excised tissue, the surgical wounds of the surgery patient remain open and proceeding with surgery is suspended (delayed) until an evaluation of the image data is received from the health care specialist by the surgeon 116.

In accordance with embodiments of the invention, the invention provides a means for accessing and viewing a large amount of image data by each of one or more viewers (health care specialists) from a variety of viewing locations, and regardless of whether those viewing locations are located proximate to, or far away from, the location of the image scanning and the surgery.

Referring to FIG. 2A, the image scanning station (ISS) 120 includes an image scanning component (ISC) 230, being software which controls the scanner 160 to perform scanning of the surface of the tissue sample 162 and storage of the scanned image data 126. The ISC 230 stores the image data into an image data set 126.

Under direction of a user (operator) of the image scanning station (ISS) performs scanning of the exposed surface of the tissue 162 at a scanning resolution that equals or exceeds a foreseeable amount of the resolution required for inspection of the tissue by a health care specialist. In some circumstances and in this use scenario, this scanning resolution is the full (highest) scanning resolution this embodiment of the scanning station is designed to scan.

In this use scenario, the ISC 230 scans at a quarter micron per data pixel resolution and generates more than 20 gigabytes of image data for one reflective channel. With currently available scanning technology, at a quarter micron data pixel resolution, the scanning would require about 25 minutes to completely scan. At a half micron data pixel resolution, the scanning would require about 6.5 minutes to scan. At a one micron data pixel resolution, the scanning would require only about 1.6 minutes to scan. While scanning the tissue 162, the scanned image data is stored onto the data storage device 124. The image scanning station 120 is attached to a high data rate access (50+ megabyte per second) data storage device 124.

In this circumstance, the mass storage device 124 is a solid state data storage device that is locally accessible and having a very high data rate of about 400 megabytes per second. A time required for scanning of the exposed surface of the tissue 162 is dependent upon the per data pixel resolution for which it is scanned. For example, in this circumstance, optical scanning of one micron data pixels would require about 1.6 minutes, for one half micron data pixels would require about 6.5 minutes and for one quarter micron pixels would require about 25 minutes. At such a high rate of data storage, storage of scanned imaged data that is 20 gigabytes in size requires only about 40 seconds of elapsed time, being less than one minute to complete.

The scanned image data is stored into an image data set via the operating system 222 executing on the image scanning station 120. The image data set file 126, also referred to herein as a data set file 126 or data set 126, resides within at least one file stored within the file system associated with the operating system 222. In total, scanning of the exposed surface of the 625 square millimeter tissue sample and the storing the resulting image data requires less than 8 minutes of elapsed time for scanning one half micron pixels, which is sufficient to display tissue at a human cellular resolution.

The data set 126 includes the scanned image data itself, and information associated with the image data, referred to herein as metadata. The metadata includes a unique identifier for the data set, a set of parameters associated with the scanning and the date and time of the performance of the scanning. The parameters of the scanning include the scanning resolution and the physical dimensions of the exposed surface of the tissue, for example.

Optionally, other associated information, such as a description of the circumstances of the surgery, body location of the tissue, identity of the scanning station and of the scanner operator, and/or of the patient, and/or of the surgeon 116 can also be stored as metadata inside of the data set.

The 20 gigabytes of image scanning data, of the exposed surface of tissue is far more information that can be displayed onto one user interface display screen (UIDS), at any one time. However, the entire exposed surface of tissue can be displayed within a user interface display window (UIDW) of a UIDS 130 at one time, if the image data is processed to create supplemental image data having one or more resolutions that are each reduced from the original full scanning resolution, so that such supplemental image data can represent larger portions of the image of the exposed surface of the tissue onto the UIDS 130 at one point in time.

Accordingly, the image scanning station (ISS) 120 also includes an image processing component (IPC) which provides the supplemental image data in order to enhance the data set in preparation for viewing. The IPC is configured to process the scanned image data to compute and create the supplemental image data that is divided into separate portions of image data, having various resolutions. These various resolutions are each different from the full resolution of originally scanned image data, and are each computed and reduced from the full resolution of the originally scanned image data, that was generated from the original scanning of the tissue 162.

FIG. 2C illustrates various resolutions of image data that can be employed for viewing a optically scanned image of the excised tissue 162. In the embodiment shown here, there are four different resolutions of image data.

The first (highest) image resolution 288, is the highest image resolution of image data 288 represented in this embodiment and in this figure, and is of the same resolution as that captured from the original scanning of the tissue 162, and is represented as a first horizontal line 288 that is drawn substantially proximate to a lower edge of this figure.

For this image data resolution, each data pixel measures 0.24 microns wide and 0.24 microns high, and is referred to herein as a one quarter micron pixel. One million of these quarter micron data pixels pack into each one of 10,000+ fields of view (frames) that can be combined to represent the image of the entire exposed and scanned surface of the tissue 162. Each display frame or field of view has a width equal to about 240 microns and a height equal to about 240 microns.

Because there is overlap between the scanning of each (frame) field of view, and where such overlap is stitched together via software to generate a complete set of image data, about 11,100 fields of view (frames) are actually scanned to stitch together and generate about 10,000 viewable (frames) fields of view of stitched image data. With current confocal optical scanning technology, it would require about 25 minutes to entirely scan the 625 square millimeter exposed surface of tissue.

However, that when scanning at one half micron data pixel resolution, about 2800 fields of view (frames) are actually scanned to stitch together and generate about 2,500 fields of view (frames) of stitched together image data. With current confocal optical scanning technology, it would require about 6.5 minutes to entirely scan the 625 square millimeter exposed surface of tissue.

And when scanning at one micron data pixel resolution, about 700 fields of view (frames) are actually scanned to stitch together and generate about 625 fields of view (frames) of stitched together image data. With current confocal optical scanning technology, it would require about 1.6 minutes to entirely scan the 625 square millimeter exposed surface of tissue.

At a quarter micron image data resolution, (about 10,000 fields of view×one million data pixels per field of view=10 billion) quarter micron data pixels that are required to represent the stitched together image of the entire exposed and scanned surface of the tissue 162, requiring more than 20 gigabytes of image data (2 bytes of image data per data pixel) to represent an image of the exposed and scanned surface of tissue that is 625 square millimeters, being about one square inch in area size.

Note that a user interface screen typically includes 2-3 million display pixels, which is far less than the 10 billion quarter micron data pixels required to view the entire set of image data at one time.

A second resolution 286, being algorithmically computed from a higher resolution of image data 288, is represented as a second horizontal line that is drawn above the first resolution 288. For this resolution of image data, each data pixel measures about 0.96 microns wide and about 0.96 microns high, and is referred to herein as a one micron pixel. One million of these one micron data pixels pack into each one of (625=25×25) fields of view that each have a width equal to about 960 microns (about one millimeter) and a height equal to about 960 microns (about one millimeter).

At this image data resolution, 625 million one micron data pixels are required to represent the entire exposed surface of the tissue sample, requiring 1.25 gigabytes of image data (2 bytes per data pixel) to represent an image of the exposed surface of tissue that is 625 square millimeters, about one square inch in area size.

A third resolution of image data 284, being algorithmically computed from either of the higher resolutions of image data 286,288 is represented as a third horizontal line that is drawn above the second horizontal line, representing the second (highest) resolution 286.

Preferably, the third resolution of image data 284, is algorithmically computed from the higher resolution of image data 286 and is represented as a third horizontal line that is shown as being drawn above the second (highest) resolution of image data 286. Alternatively, in other embodiments, this third resolution of image data 284 can be computed from the image data of higher resolution 288.

At this image data resolution, each data pixel represents an area of tissue that measures about 4.8 microns wide and about 4.8 microns high, and is referred to herein as a five (5) micron data pixel. One million of these five micron data pixels pack into each one of 25 UIDS fields of view, also referred to herein as viewing fields of view within a five (5) row by five (5) column matrix including (25) viewing fields of view. Each viewing field of view within this matrix representing an area of tissue having a physical width equal to about 4800 microns (about 5 millimeters) and having a height equal to about 5000 microns (about 5 millimeters) of tissue.

At this image data resolution, 25 million one micron data pixels are required to represent the entire exposed surface of the tissue sample, requiring 50 megabytes of image data (2 bytes per data pixel of image data) to represent an image of the exposed surface of tissue that is 625 square millimeters, which is approximately one square inch in size.

Preferably, the fourth resolution 282 of image data is algorithmically computed from the higher resolution 284 of image data and is represented as a fourth horizontal line that is shown as being drawn above the third horizontal line representing the third (highest) resolution 284 of image data. Alternatively, in other embodiments, this fourth resolution 282 of image data can be computed from the image data of higher resolution 286 or of higher resolution 288.

At this image data resolution, each data pixel measures about 24 microns wide and about 24 microns high, and is referred to herein as a twenty-five (25) micron data pixel. One million of these twenty-five micron data pixels pack into just one UIDS field of view, being a viewing (viewable) field of view within a matrix having just one row and just one column. This one UIDS viewing field of view representing an area of tissue being the entire exposed surface of excised tissue. This one viewing field of view representing tissue having a width equal to about 25000 microns (25 millimeters) and a height equal to about 5000 microns (5 millimeters).

At this image data resolution, 1 million one micron data pixels are required to represent the entire exposed surface of the tissue sample, requiring 2 megabytes of image data (2 bytes per data pixel of image data) to represent an image of the exposed surface of tissue that is 625 square millimeters, which is approximately one square inch in size.

The algorithmic computation for each computed image resolution is performed via a down resolution sampling procedure, also referred to herein as "down sampling", where information from a plurality of higher resolution pixels is consolidated into and represented by (1) representative data pixel in a lower resolution.

The above set of cascading resolutions provides additional options for a viewer to view the image data. These additional options enable a viewer of the image data to more flexibly choose a viewing path through the image data to efficiently perform an inspection and evaluation of the image data. This feature of the invention is further described within FIGS. 3A-3F.

FIG. 2D illustrates a simplified representation of an embodiment of the image viewing station (IVS) 150. In this embodiment, the image viewing station (IVS) 150 includes much of the same type of hardware as the image scanning station (ISS) 190. The IVS 150 has hardware including a keyboard, a mouse (screen pointer) device, and user interface display screen (UIDS) 292. The UIDS 292 is configured to display at least one user interface display window (UIDW).

As for software, the IVS 150 is installed with a Windows operating system (OS) software, and preferably a Windows 10 operating system software. The operating system (OS) including device drivers to interface with hardware peripherals that are attached to the IVS 150. The IVS 150 is installed with software application programs, including an image viewing component (IVC) 152 and including at least one web browser program, being preferably a Google Chrome browser program.

Unlike the image scanning station 190, the image viewing station (IVS) 150 does not necessarily have an attached scanner device and does not necessarily have an attached large capacity and/or high data rate mass storage device 224. However, the IVS 150 could have some of all of such extra hardware and furthermore, could be designed as both an image scanning station 190 and as an image viewing station 150.

In this embodiment, a web browser program executes in the virtual memory of the IVS 150, and interoperates with an operating system that is installed onto the IVS 150. A user of the IVS 150 interacts with the web browser to gain online access to an Internet web server, referred to as an Image Access Portal (IAP) 140 that is hosting an Output image access component (Output IAC) 142.

Upon the IVS 150 gaining online access to the Output IAC 142, the Output IAC 142 lists one or more image data sets 126 that are currently available for viewing by the user of the IVS 150. These one or more image data sets 126 can be each located at separate locations that are not proximate to each other. Upon the user selecting a data set for viewing, an image viewing component (IVC) 152 is downloaded as software from the Output IAC 142 into a web browser program executing on the IVS 150. The IVC 152 is designed to provide an interactive user interface for viewing of image data, where the user of the IVS 150 communicates viewing directives to the IVC 152, and in response, the IVC 152 receives and responds to those viewing directives, often via communication with the Output IAC 142. A further description of the IVC 152 is shown in FIGS. 3A-3F.

Preferably, and in this embodiment, the IVC 152 includes a modified version of the publically available Open Sea Dragon (OSD) software (OSDS). The OSD software is implemented as open source code and is written in Java script and HTML. The OSD software is not compiled into executable machine instructions prior to runtime, but is instead interpreted during runtime.

The publically accessible and un-modified version of the OSD software is designed to access image data that is stored within a local file system that is associated with an operating system upon which the OSD software is executing. Such an arrangement typically yields higher data rate access to the image data than access of such image data over a local area or wide area network. Having, such high data rate access to the image data enables the OSD software to respond more quickly to the user of the OSD software while the user interacts with the OSD software.

However, in accordance with the design of the invention, and in accordance with the circumstances within which the invention is designed to operate, there is no one set of image data to be accessed and viewed over time. Instead a plurality of individual image data sets 126 are each physically stored at a variety of different and remote locations relative to the location of a computer upon which the OSD software executes. Via embodiments of the invention, each image data set is created, typically during surgery, and becomes available for access and viewing, typically for a limited period of time, and typically for the duration of the surgery.

Upon completion of the surgery, the image data set can be transferred to an alternative data storage device that is located physically apart and away from the data storage device 124 that originally stored the image data set and that is directly accessible to the image scanning station (ISS) 120. Such alternative data storage can function as long term data storage for sets of image data after surgery. Such alternative data storage would not necessarily be required to be accessible to the image scanning station (ISS) 120 originally storing the set of image data.

However, as shown in FIGS. 2E and 2F, such long term data storage could be made accessible from an image transfer station (ITS) 170 via a local area network or via more direct and higher speed data access. The ITS 170 would include hardware like the image scanning station (ISS) 120, except that it would not be required to attach to image scanning hardware and not be required to execute image scanning or processing software 232. The ITS 170 would be executing Intermediate image access component (Intermediate IAC) software 172 and would not necessarily require a local and/or high speed access to a mass storage device. Optionally, the ITS 170 could access large amounts of image data via a local area network. Optionally, the ITS 170 could possess Input image access component (IAC) functionality within the Intermediate IAC 172 to detect access availability and un-availability of stored image data over time.

Note that an alternative image access pathway of communication could be established between the Output IAC and the alternative data storage device. In some circumstances, an Intermediate IAC 172 executing on an image transfer station (ITS) 170 is configured to have direct access to the alternative data storage device, and is configured to operate within a set of IACs that are configured to form this alternative image access pathway of communication.

Because of data storage limitations of an image scanning station (ISS) 120, each originally stored image data set is eventually removed from the data storage device 124 of the ISS 120. If the originally stored image data set is removed, then the original image access pathway of communication between the Output IAC and the originally stored image data is terminated. Also, the system can be configured to terminate the original image access pathway of communication with or without removal of the originally stored image data from the data storage device 124 of the ISS 120.

During normal operation, each image data set suddenly becomes available for viewing at a first location and at a first time, typically during the performance of surgery, and later, suddenly becomes unavailable for viewing, at least at that first location or unavailable for viewing at any location. The timing of the events of a set of image data becoming available and then becoming un-available, and possible becoming available again while stored at a second location, generally occur in a manner that is not scheduled over time. As a result, the location and/or timing of such events are generally not pre-determined by the over time.

Note that when a set of image data becomes available, an image access pathway of communication is referred to herein as being activated. When that set of image data becomes un-available, the image access pathway of communication is referred to herein as being terminated.

In typical circumstances, the Output IAC 142 is located remotely from where the image data 126 is stored, and as a result, the Output IAC 142 has no high data rate access to the stored image data. To access the remotely located image data, wherever it may reside, the Output IAC 142 communicates with other members of a set of image access components to locate and to access the image data 126. The set of image access components are linked into a network of interoperating image access components, where each image access component has a parent and/or child relationship with at least one other image access component within the set of image access components. How the image data is relayed between the IAC's is described in more detail in association with FIG. 2E.

In accordance with some embodiments of the invention, the Open Sea Dragon (OSD) software is modified to access image data that is located not within a file system that is local (directly accessible) to a computer upon which the OSD software is executing, and not local (directly accessible) to a computer from which the OSD software has been downloaded from. Instead, the OSD software is modified to access image data by employing a set of image access components (IACs), including an Output IAC 142 and other types of IACs.

The OSD software employs the set of IACs via communication with an Output IAC 142, which is accessible to the OSD software via a wide area network, such as the Internet. Preferably, the Output IAC 142 is executing upon a computer, referred to herein as an image access portal (IAP) 140, that is designed to be located remotely from where the image data could be stored and located remote from where the IVS could be located.

In accordance with the embodiments of the invention, the OSD software is modified, and downloaded from the Output IAC 142 that is executing on an Image Access Portal (IAP) 140, and embedded into an image viewing component (IVC) 152. The IVC 152 being a set of software including one or more processes. The OSD software is modified to NOT access data from a file system that is local to the computer upon which the OSD software is executing, and is instead designed to communicate an http get request function call to a URL of software being the Output IAC 142 that is executing on the IAP 140, to access various sets (portions) of image data that are stored on one or more computers that typically reside at locations that are remote from the IVC 152.

The http get request is implemented as a function call that enables the IVC 152 and the downloaded, modified and OSD software that is embedded into the IVC 152, to access image data via Output IAC 142, while the Output IAC 142 interoperates with a set of image access components (IACs), to access the various sets (portions) image data from whatever locations such image data may reside, at that particular time. In other words, the image data to be accessed is subject to being moved and/or copied to new locations over time, especially after completion of the surgery that originally produced the image data.

In some embodiments, the Output IAC 142 spawns a separate Web Tile Server (WTS) process. The Output IAC 142 software, like any other IAC software, is implemented a set of one or more processes and/or portions of a process executing upon a computer, and preferably executing within an operating system environment on that computer. The WTS is a process that is designed to communicate the request for the sets (portions) of image data to a first other IAC that has previously registered with the Output IAC 142 as a child of the Output IAC 142 and that has previously registered with the Output IAC 142 as having access to the requested sets (portions) of image data.

The WTS process software functions as a portion of the Output IAC 142 software. The aforementioned "first other IAC" is referred to herein as a child IAC of the Output IAC 142. This child IAC can either be configured either as an Intermediary IAC 172 or as an Input IAC 122 within a chain of IAC's. This chain of IAC's includes at least the one Output IAC 142 at a first end of the chain of IAC's and includes an Input IAC 122 at a second end of the chain of IAC's. This "first other IAC" that is a child IAC of the Output IAC 142 is referred to herein as the "first child" IAC of this chain of IACs.

If the first child IAC is not an Input IAC 122 and if it does not have access to the requested image data, it is designed to re-communicate the request for the sets (portions) of image data to a second other IAC that has previously registered as a child IAC of this first child IAC and that has previously registered as having access to the requested sets (portions) of image data. This first other IAC will be referred to herein as the "second child" IAC.

The request for sets (portions) of image data along a chain of IAC's is communicated (relayed) along the chain of IAC's until an Input IAC 122, previously registered as having access to the requested sets (portions) of image data and registered as a child IAC to another IAC in the chain of IAC's between the Output IAC 142 and the Input IAC 122, receives the request for the sets (portions) of image data. In other words, this particular chain of IACs, which may form a subset of IAC's with a larger network of IACs, has been previously configured via previous registration, to provide access to this particular set of image data being requested.

Upon receiving the request for the sets (portions) of image data, the Input IAC 122 communicates the requested image data in the form of image data tiles all the way back through the chain of IAC's to the Output IAC 142, which delivers the requested image data to the OSD software operating within the image viewing station (IVS) 150.

Referring back to the unmodified version of the OSD software, it is designed to be downloaded to a web browser from an OSD web server and is further designed to access image data via a function call to access files from within a file system that is linked (local) to a computer upon which the OSD web server software executes. In other words, unlike embodiments of the invention, this file system is linked to an executing instance of an operating system upon which the unmodified version OSD web server software executes.

Conversely, embodiments of the invention employ a modified version of the OSD software and are designed to access files from a file system that is linked (local) to a computer upon which a particular IAC within the chain of IACs, executes. This particular IAC has access to, and direct access to, the image data being requested in relation to other IACs within the chain of IACs.

An IAC that is able (configured) to access (reach) the requested image data without being required to communicate through another IAC, is referred to herein as an IAC having direct access to the requested image data. An IAC that is required to communicate through another IAC to access the requested image data is referred to herein as having indirect access to the image data. In some circumstances, an Intermediary IAC 172, as opposed to an Input IAC 122, is the particular IAC within the chain of IACs having direct access to the requested image data.

FIG. 2E illustrates a simplified representation of an embodiment of a system including a tree type of hierarchy among image access components. A set of image access components are collectively configured to provide remote access to an image data set from an image scanning station (ISS) 120*a* to one or more image viewing stations (IVS) 150*a*-150*c*.

As shown, multiple image scanning stations (ISS) 120*a*-120*n* are located within a second health care facility 210. Each ISS 120*a*-120*n* includes a locally accessible mass storage device (not shown here) upon which scanned image data is stored. An image data that is obtained from each scanning of excised tissue, along with associated supplemental (computed) image data and metadata, are stored within an image data set file 126*a* onto this mass storage device 124*a*, directly attached to image scanning station 120*a*.

An Input image access component (IAC) 122*a*-122*n* each respectively resides and executes within the image scanning stations (ISS) 120*a*-120*n*, within the health care facility 210. Each Input IAC 122*a*-122*n* is configured to periodically detect a presence of one or more data sets created and/or currently stored within the mass storage device 124 of the image scanning station (ISS) 120*a*-120*n*. Essentially, each Input IAC 122*a*-122*n* "takes inventory" of the presence of any image data set files that are accessible to the IAC 122*a*-122*n* and that appear to be available for viewing. When available for viewing, these image data set files include an amount of scanned image data, associated supplemental image data and metadata information that is determined by the Input IAC 122 to be complete and ready for viewing.

Each Input IAC 122*a*-122*n* is configured to operate as a child image access component (IAC) only, within a linked hierarchy of image access components. Each Input IAC 122*a*-122*n* is configured to link to one parent IAC, being in this circumstance, an Intermediate IAC 172, which is shown to reside and execute on a separate computer, also referred to herein as an image transfer station (ITS) 170 within the same health care facility 210.

The Intermediary IAC 172 is configured to operate as both a child IAC and as a parent IAC. The intermediary IAC 172 is configured to operate as a parent to each of the multiple Input IAC's 122*a*-122*n* within the health care facility 210, and is also configured to operate as a child IAC in relation to the Output IAC 142, which resides and executes on a computer, referred to herein as an image access portal (IAP) 140 that is Internet network accessible and that is located outside of the health care facility 210.

Image viewing stations (IVS) 150*a*-150*b*, being Internet network accessible computers, such as a desktop computer for example, are located within the first health care facility 210. Likewise, one or more other image viewing stations, including such as IVS 150*x* for example, are located outside of the first healthcare facility 210 and are instead located in another third health care facility 280, that is located miles away from the first health care facility 10. All of these image viewing stations (IVS) 150*a*-150*x*, can access image data from one or more image scanning stations, via online Internet access to the Output IAC 142 of the image access portal (IAP) 140.

In one use scenario, a user of the system, such as a pathologist, for example, receives a notification of image data being available for viewing, via a communication such as a mobile phone text message and or via electronic mail correspondence, for example. The communication includes a web site address and unique identifier of an image data set 126*a* that has just recently become available. The method of this communication is referred to herein as a notification path of communication. The image data set 126*a* includes scanned and associated supplemental image data, and includes an image data set associated metadata information such as name of health care facility, type of surgery, name/identifier of the surgeon 116 and of the patient, for example.

In response, the user online accesses the Internet website of the Image Access Portal (IAP) 140 that is associated with an Output image access component (IAC) 142, logs onto the website of the Image Access Portal (IAP) 140 by authenticating himself or herself via communication of at least a user name and password.

In response, the Output IAC 142 displays a list of accessible image data sets that have been previously communicated from other IAC's that are linked as children of the Output IAC 142. The Output IAC 142 searches the list, and displays a listing of one or more image data sets along with their unique identifiers, to the user.

In response to displaying a list of image data sets, the user selects for viewing, the image data set 126*a* associated with unique identifier of the image data set 126*a* that is listed inside of the mobile phone text message, and also listed on the IAP 140 upon successfully logging into the IAP 140.

In response to the selection by the user, the Output IAC 142 communicates image viewing component (IVC) 152 software to a browser program executing on the image viewing station (IVS) 150*x*. In this embodiment, the IVC 152*x* is implemented in Java Script that is down loaded from the IAP 140 website.

Also in response the selection by the user, the Output IAC 142 communicates a request to receive a first portion of the content of the selected image data set 126*a*, referred to the image data set of interest, to a child IAC, in this circumstance the Intermediary IAC 172, that had previously communicated the availability of access to the image data set of interest 126*a*, to the Output IAC 142.

The Intermediate IAC 172 searches its list of accessible (available) image data sets, the identity of which had been previously communicated from other IAC's that are linked as direct or indirect children of the Intermediate IAC 172. Upon finding the image data set 126 of interest 126*a* that is being selected by the user, the Intermediate IAC 172 communicates a request to communicate the first portion of the content of the image data set 126 of interest to a child IAC, in this circumstance being the Input IAC 122*a*, that had previously reported the availability of access to the image data set of interest 126*a*.

In response to the Input IAC 122*a* receiving the request from the Intermediate IAC, the Input IAC 122*a* communicates the first portion of the content of the image data set of interest 126 to the Intermediate IAC 172. Next, the Intermediate IAC 172 relays (communicates) the first portion of the content of the image data set 126 of interest to the Output IAC 142. Next, the Output IAC relays (communicates) the first portion of the content of the image data set 126 of interest 126*a* to the image viewing component (IVC) 152*x* of the image viewing station (IVS) 150*x*.

In this use scenario, the Input IAC 122 has been in possession of the image data set of interest since its creation. The Input IAC 122*a* previously reported the existence and accessibility of the image data set 126*a* to the Intermediate IAC 172 upon completion of scanning, processing and storing the image data set of interest 126*a*, into its locally accessible mass storage device 124*a*. In response to receiving communication regarding the availability of the image data set 126*a*, the Intermediate IAC 172 relays the communication regarding the image data set of interest 126*a* to its parent IAC, being the Output IAC 142.

At some time in the future, the image data set of interest will be removed from the mass storage device of the image scanning station from which it was created. Such an image data set removal event will be reported by the Input IAC 122*a* to the Intermediate IAC 172, and such an image data removal event will be relayed and reported by the Intermediate IAC 172 to the Output IAC 142. Upon receiving the report of the removal event, each of the Intermediate IAC 172 and the Output IAC 142 removes the information regarding the removed (unavailable) image data set 126*a* from its list of accessible (available) image data sets 126.

FIG. 2F further illustrates operation of a set of image access components shown in FIG. 2E. These access components are collectively configured to provide remote and rapid access to an image data set from an image scanning station (ISS) 120*a* to an image viewing station (IVS) 150*x*.

When the user of the image viewing component (IVC 152*x* enters a viewing directive, the IVC 152*x* optionally communicates an image access request 250, which includes a set of image access parameters, via a communication 250 to the Output IAC 142. The image access parameters define image data via location and resolution attributes of the image data within the entire repository of image data within a particular image data set of interest. The image access parameters typically identify image data that is typically being stored as a portion of the entirety image data being stored within a particular image data set of interest.

In response to receiving the image access request 250, the Output IAC 142 checks to see if it has cached all or some or all of the image data that satisfies the image access request 250. If the cached image data cannot satisfy the entire image access request 250, then the Output IAC 142 communicates an image access request 252 to a child IAC, being an Intermediate IAC 172, that has previously reported the availability for access of the image data set 126*a* of interest to the Output IAC 142.

The image access request 252 including image access parameters that define a remainder, being the difference between image data defined by the image access request 250 and the image data that is currently being cached within the Output IAC 142, Alternatively, if the Output IAC 142 can satisfy the image access request in its entirety, then it, the output IAC 142 responds by communicating an image transfer transaction 264, including image data that entirely satisfies the image access request 250, to the image viewing component (IVC) 152*x*.

In accordance with the invention, when a child IAC reports an availability for access of a particular image data set of interest to a parent IAC 142, such a reporting action also indicates to the parent IAC 142 that the child IAC 172 has access to, and can deliver image data from the image data set of interest, in response to receiving a request for access by its parent IAC 142.

In response to receiving the image access request 252, the Intermediate IAC 172 checks to see if it is currently caching image data that entirely satisfies some or all of the image access request.

If the currently cached image data cannot satisfy the entire image access request 250, then the Intermediate IAC 172 communicates an image access request 254 to a child IAC, being the Input IAC 122*a*, that had previously reported the availability for access of the image data set 126*a* of interest to the Intermediate IAC 172.

The image access request 254 including image access parameters that define a remainder, being a difference between image data defined by the image access request 252 and the image data that is currently being cached within the Intermediate IAC 172.

Alternatively, if the Intermediate IAC 172 can satisfy the image access request in its entirety, then it,the Intermediate IAC 172 responds by communicating an image transfer transaction 262, including image data that entirely satisfies the image access request 252, to the Output IAC 142.

In response to receiving the image access request 254, the Input IAC 122*a* checks to see if it is currently caching image data that entirely satisfies the image access request.

If the currently cached image data cannot satisfy the entire image access request 254, then the Input IAC 122*a* retrieves image data that is sufficient to entirely satisfy the image access request 254, from an image data set file 126*a* that is being stored onto a mass storage device 124*a* and that is accessible to the Input IAC 122*a*. The Input IAC 122*a* then responds by communicating an image transfer transaction 260, including image data that entirely satisfies the image access request 254, to the Intermediate IAC 172.

In response to receiving the image transfer transaction 260 from the Input IAC 122*a*, the Intermediate IAC 172 communicates an image transfer transaction 262 to the Output IAC 142 that includes image data that entirely satisfies the image access request 252.

In response to receiving the image transfer transaction 262, the Output IAC 172 communicates an image transfer transaction 264 to the Image Viewing Component (IVC) 152*x*, that includes image data that entirely satisfies the image access request 250.

In response to receiving the image transfer transaction 264, the image viewing component (IVC) 152*x* performs the viewing directive received from the user and that originally prompted the communication of the original image access request 250 from the IVC 152*x* to the Output IAC 142.

Note that in the above described tree hierarchy of FIGS. 2E and 2F, the Output IAC 142 indirectly communicates with the Input IAC 122*a* via the Intermediate IAC 172. Alternatively, if hypothetically, there was no Intermediate IAC 172 disposed in between the Output IAC 142 and the Input IAC 122*a*, then the Output IAC 142 would directly communicate with the Input IAC 122*a*.

In accordance with the invention, a hierarchy of image access components are not required to include an Intermediate IAC 172. And furthermore, with respect to embodiments employing an Intermediate IAC 172, the invention does not limit such embodiments to including just one Intermediate IAC being disposed between an Output IAC 142 and any one Input IAC. In some embodiments, a series of a plurality (more than one) intermediate IACs can be disposed between the Output IAC and anyone Input IAC.

For example, with respect to a tree hierarchy of IACs having 10 Input IACs, each of these Input IACs could directly link or indirectly link to the one Output IAC 142, acting as a root node of this tree hierarchy. A series of IACs located along a path between the Output IAC and each Input IAC is variable and could include zero, one or more Intermediate IACs 172. In other words, there is no requirement that any number of Intermediate IACs 172 that reside between an Output IAC 142 and any one particular Input IAC 122 be the same between that Output IAC and any other particular Input IAC.

Also note that if a set of image access components (IACs) include an Output IAC and optionally one or more Intermediate IACs, each having one and only one child IAC, then this arrangement is referred to herein as a chain type of hierarchy of IACs, and would include one and only one Input IAC 122. And if this set IACs includes one and only Input IAC 122 and no Intermediate IACs 172, then this hierarchy would be referred to as a chain type of hierarchy having only two nodes, being the smallest and most simple type of hierarchy of a set of IACs.

Figure 3A:
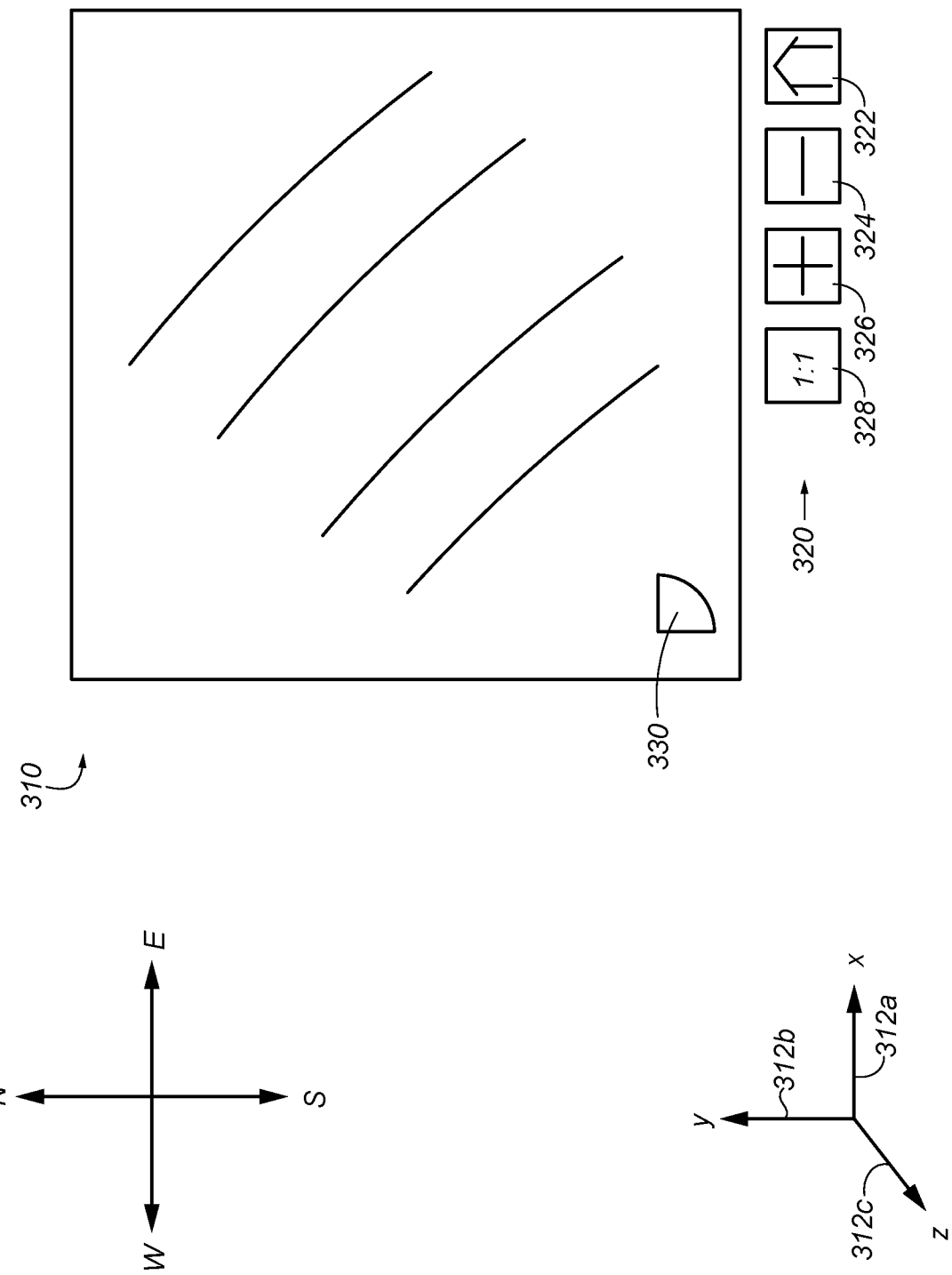
FIG. 3A illustrates a simplified representation of a user interface window of an image stream viewing component (ISVC) displaying image data.

FIG. 3A illustrates a simplified representation of image data as displayed within a user interface display window (UIDW) 310 of an image viewing station (IVS) 150. As shown in this embodiment, a user interface display window 310 is square in shape and displays image data representing the exposed surface of an ex-vivo tissue sample that was just recently excised (cut) from a patient during surgery, and then optically scanned to create the image data shown here.

In this example use scenario, the performance of surgery upon the surgery patient is currently being suspended, while the patient waits upon an operating room table and while the surgeon 116 waits for an evaluation of the optically scanned tissue by another health care specialist. The IVS 150 is located about 20 miles from the location of where the surgery is currently being performed.

In this example, the exposed surface of the ex-vivo tissue sample is square in shape and measures 25 millimeters by 25 millimeters. This exposed surface, representing a cross-section of the tissue sample, is a surface that is oriented substantially parallel to the drawing surface of this figure, and which is oriented substantially parallel to a two dimensional plane defined by the X axis 312a and the Y axis 312b shown here. The Z axis 312c is directed perpendicular to the X 312a and Y 312b axes, and is also directed perpendicular to the planar drawing surface of this figure.

In this embodiment, the UIDW 310 has a physical size measuring 10 inches and 1000 display pixels along the X axis 312 and 10 inches and 1000 display pixels along the Y axis 312b. Accordingly, the user interface display screen (UIDS) pixel density, also referred to herein as the linear pixel density of the UIDW screen, is 100 pixels per inch in a direction that is parallel to the X axis 312 and 100 pixels per inch in a direction that is parallel to the Y axis 312b.

The fourth (highest) resolution 282 of the image data as shown is referred to herein as an initial view or "macro-view" of the image data. The magnification/resolution of this view of the image data is the lowest resolution of the (4) pre-configured resolutions provided by this embodiment of the invention. A macro-view displays the entire exposed surface of the excised tissue within the UIDW 310. The image data being viewed here is includes twenty-five (25) micron image data pixels, are in accordance with that of the lowest resolution of image data, which was computed from the image data obtained from the originally scanning of the exposed surface of the tissue sample, as described in association with FIG. 2C.

The initial macro-view shown here is somewhat similar to what could be seen from the human eye with the assistance of a magnifying glass. As shown here, this resolution includes UIDW display pixels that each represent a physical area of tissue that is square in shape and that measures 25 microns in width and 25 microns in height. The macro-view shown here is shown in grayscale with no color enhancement. However, depending on how the tissue sampled was originally scanned, this initial macro-view can alternatively be shown in greyscale and/or optionally with some additional color enhancement.

A set of user interface controls 320 are disposed on the UIDS 310 and just below the UIDW 310. These controls include a resolution reset button 322, a DOWN magnification button 324, and UP magnification button 326 and an image resolution status indicator 328. Pressing the down magnification button 324 reduces the resolution of the view of image data to a next lowest pre-computed resolution. Pressing reset resolution button 322 restores the view of the image data to the lowest pre-computed image resolution, being the initial view or macro view.

Because the physical size of the UIDW 310 is 10 inches by 10 inches, and the exposed surface of the excised tissue is 1 inch by 1 inch, this macro-view is in effect, a 10 to 1 linear magnification of what could be seen with the un-aided human eye while examining the exposed surface of the excised tissue. A row of user interface controls 320 are located below a bottom edge of the UIDW 310.

The function of these viewing directive controls are explained in the following text.

In this use scenario, a portion of the displayed image data appears to be some sort of lesion 330, also referred to herein as the lesion of interest. The user of the IVS 150, being a pathologist and the viewer of the image data, desires to obtain a closer view of this portion, being the lesion 330 of the exposed surface of the tissue sample.

FIG. 3B illustrates communication of a first viewing directive from the user of the image viewing station (IVS). As shown, a location within the UIDW 310, represented by a UIDW location 332, is associated with the first viewing directive and is also indicated by an intersection of the cross-hair lines 332a-332b.

To communicate the viewing directive, the user aims a mouse pointer of a mouse device of the IVS 150 at a first UIDW location 332 within the UIDW 310, being the lesion of interest, and presses and holds a left hand button on the mouse device and drags the image in a northeasterly direction 334. If the IVS 150 includes a touch screen, then the viewing directive can be performed via touchscreen input, such as via using fingers to pinch/drag the image in the northeasterly direction 334.

The image is dragged and relocated so that the lesion of interest is re-located to a second location, being a center point location 338 within the UIDW 310. The first UIDW location 332 is positioned about 60 pixels east of the left hand side of the 310 and about 50 pixels north of the lower edge of the UIDW 310. This particular first UIDW location 332 is also represented as UIDW location coordinates (60, 50).

Figure 3C:
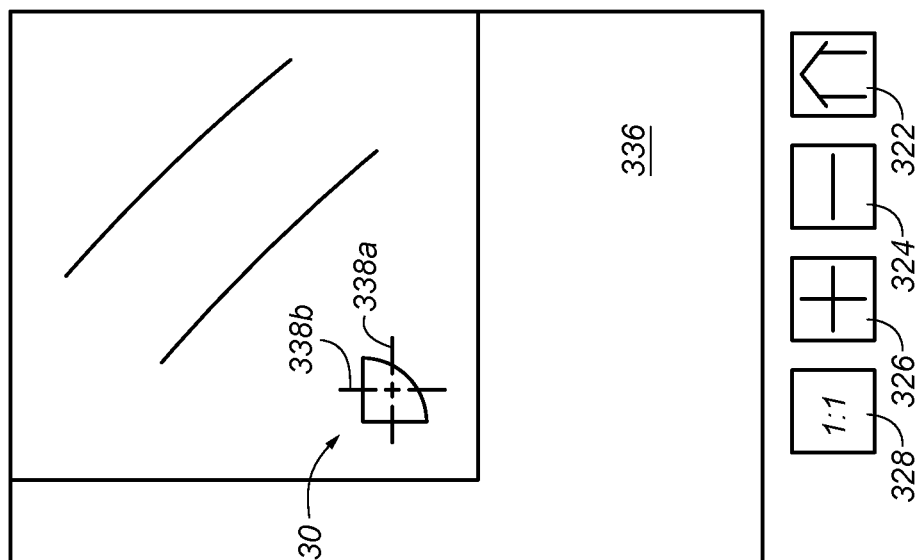
FIG. 3C illustrates updated content of the viewing window in response to the coordinate (go to) directive of FIG. 3C.

In response to communication of the viewing directive, image viewing component (IVC) software executing within the image viewing station (IVS) 150 inputs and processes the viewing directive, and in response, evaluates whether additional image data is required to process the viewing directive, and if necessary, requests and receives additional image data via the Output IAC, and if necessary, modifies the image data content inside of the UIDW 310 in accordance with the viewing directive, as shown in FIG. 3C.

FIG. 3B and 3C illustrate processing of the first viewing directive communicated from the user. In response to processing the first viewing directive, the image data content of the UIDW 310 is shifted (panned) towards a north-easterly direction so that the data pixel location 332 within the image data is now re-located to a center display pixel location 338 within the UIDW 310, at UIDW coordinate location (500, 500).

The display pixels of FIG. 3C that are located more than 60 pixels west and/or located more than 50 pixels south of the UIDW 310 display pixel location 338, are now defining an area (portion) 336 of the UIDW 310 displaying no image data. The pixels residing in this area 336 are displayed as one uniform color. In this embodiment, the uniform color is black. The image data displayed in FIG. 3C is a cropped subset of the image data displayed in FIGS. 3A-3B. No additional image data beyond the image data displayed within FIGS. 3A-3B is required to display the image data of FIG. 3C, in response to the viewing directive of FIG. 3B.

Essentially, this first viewing directive modifies a location within the image data that is to be viewed at the center location of the UIDW 310. This viewing directive is a location type of viewing directive, as opposed to a magnification type of viewing directive, where display of particular image data is shifted relative a location within the UIDW 310.

Figure 3D:
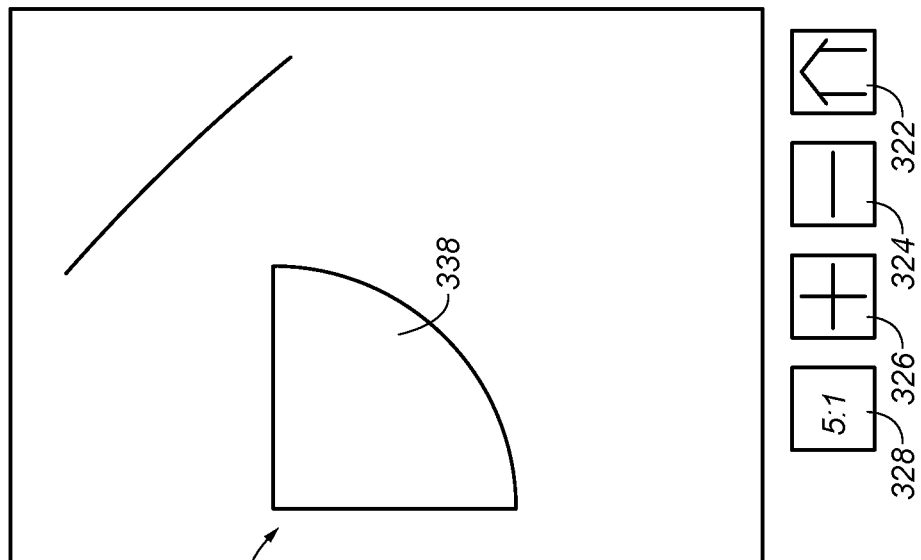
FIG. 3D illustrates a horizontal perspective view of the image data viewed inside of the viewing window of FIG. 3D.

FIG. 3D illustrates processing of a second viewing directive communicated from the user of the image viewing station (IVS). In this use scenario, the user now desires a higher magnification (higher resolution) view of the image data within the UIDW 310 relative to the view of the image data being displayed within FIG. 3C. As shown in FIG. 3C, the lesion 330 was re-located to a center location 338 within the UIDW 310.

To increase magnification of image data being viewed inside of the UIDW 310, the button labeled "+" 326, also referred to as the "UP" magnification button, is pressed by the user. In response, the content of the UIDW 310 is modified to show a magnified portion of the image data being viewed, where that portion of image data to be magnified is located around the center point location 338 of the UIDW 310. This first pressing of the UP magnification button 326 increases the linear magnification factor of the image data being displayed from (1 to 1) to (5 to 1), which corresponds to the third highest resolution 284 of image data of FIG. 2C.

In other words, a pressing of the "UP" magnification button 326 does not modify a location of the portion of the image data to be magnified, and a center location of the portion of the image to be magnified remains located in the center location of the UIDW 310. In this embodiment, the amount of magnification of the image data to be viewed, for each pressing of the UP magnification button 326, represented as a magnification factor, is configured into the system. In some embodiments, the magnification factor is configured into system as a configuration variable within the Open Sea Dragon (OSD) Java script code.

A sequence of UP magnification button 326 presses, transition the magnification factor of the UIDW 310, represented as a linear magnification factor, from a minimum magnification factor (macro-view magnification), to a maximum (highest) magnification factor. Prior to any pressing of the UP magnification button 326, the magnification factor is indicated as being equal to a one to one (1:1), being the lowest magnification factor and resolution that is provided by the system within this embodiment.

A first pressing of the UP magnification button 326, increases the magnification factor to equal (5 to 1), which corresponds to the second lowest (third highest) magnification factor 284 and resolution 284 among the (4) pre-configured magnification factors/resolutions 282-288 of image data provided in this embodiment of the system of the invention.

A linear magnification factor equal to (5 to 1) means that a portion of tissue cross-section is magnified 5 times along each of its width dimension and of its height dimension, while being displayed inside of the UIDW 310.

This linear magnification factor equal to (5 to 1) is equivalent to an area magnification factor equal to (5×5=25) twenty-five, being a magnification factor for a two dimensional area of the tissue cross-section being displayed inside of the UIDW 310.

In other words, the area of tissue that is being viewed through the entire UIDW 310 at this magnification level, also referred to herein as a user interface display (UIDS) field of view, or display field of view, represents an area that is at most, ¹⁄₂₅ of the entire size of the 25 mm square tissue cross-section that was scanned.

At this magnification level, each pixel within the UIDW 310 represents a square area of tissue that is about (4.8) "five" microns high by (0.48) "five" microns wide in size, instead of being (24.0) "twenty-five" microns by (24.0) "twenty-five" microns in size, as shown in FIGS. 3A-3C. At this magnification level, the user receives a higher resolution view of tissue surrounding the lesion 330 as well as of the lesion itself, as compared to the lower resolution view of FIGS. 3A-3C.

Note that in some embodiments, an amount of image data communicated to the IVC 152 in response to receiving a viewing directive from the user of the IVS 150 is limited to a window full of display pixels. In this circumstance, a window full of display pixels is equal to about a 1000×1000 matrix of display pixels, equaling about 1 million display pixels. In other embodiments, the IVC 152 may "look ahead" and request access to a window full plus additional display pixels in anticipation of future viewing directives to be communicated from the user of the IVS 150.

Figure 3E:
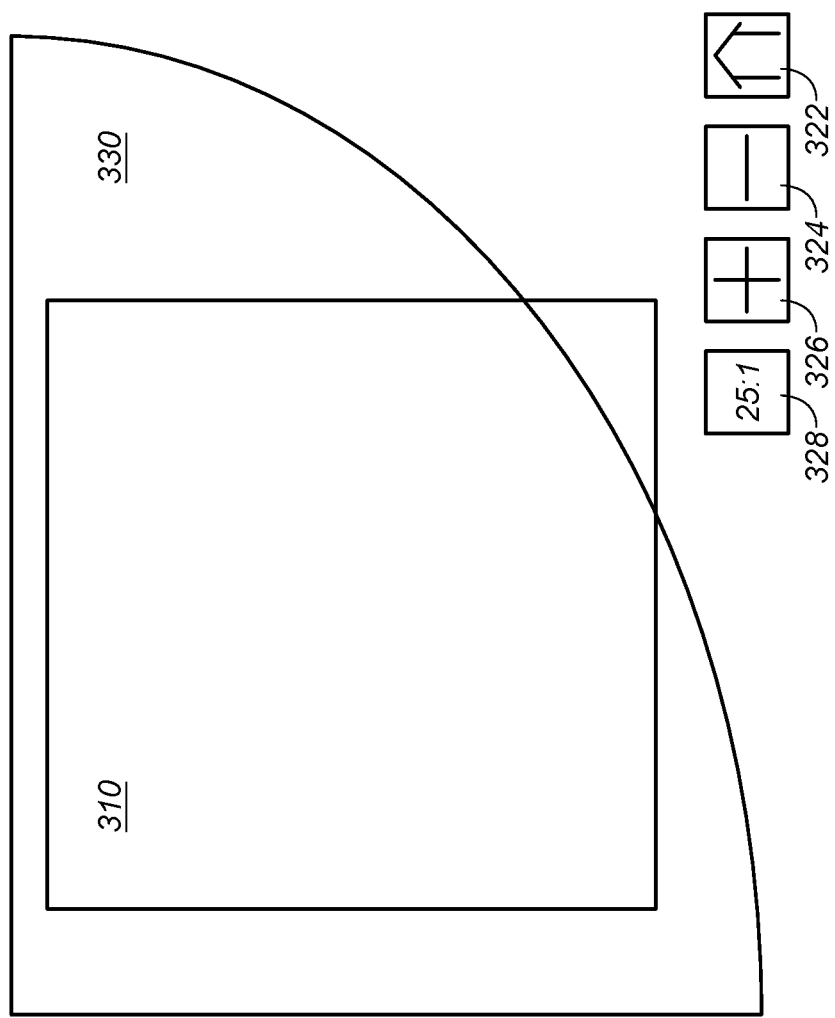
FIG. 3E illustrates updated content of the viewing window in response to a magnification (reduction) directive of FIG. 3D.

FIG. 3E illustrates processing of a third viewing directive that is communicated from the user to the IVS 150. This third viewing directive causes modification to the view of the image data that is displayed within the UIDW 310, in response to processing the third viewing directive. In this scenario, the user now desires a higher magnification (higher resolution) view of the image data in the UIDW 310 than the view of image data being displayed within FIG. 3D.

To again increase magnification of image data being viewed inside of the UIDW 310, the button labeled "+" 326, also referred to as the "UP" magnification button, is pressed by the user. In response, the content of the UIDW 310 is modified to show a magnified portion of the image data being viewed, where that portion of image data to be magnified is located around the center point location 338 of the UIDW 310.

A second pressing of the UP magnification button 326 increases the linear magnification factor of the image data being displayed from (5 to 1) to (25 to 1), which corresponds to the second highest resolution of image data 286 of FIG. 2C.

A linear magnification factor equal to (25 to 1) means that a portion of tissue cross-section is magnified 25 times along each of its width dimension and its height dimension, relative to the initial macro-view resolution equal to 1 to 1, while being displayed inside of the UIDW 310.

This linear magnification factor equal to (25 to 1) is equivalent to an area magnification factor of (25×25=625), being a two dimensional magnification factor for an amount of area of the tissue cross-section being displayed inside of the UIDW 310.

In other words, the area of tissue that is being viewed through the entire UIDW 310 at this magnification level, also referred to herein as a display field of view, represents an area that is at most, 1/625 of the entire size of the 25 mm square tissue cross-section that was scanned. At this magnification level, each pixel within the UIDW 310 represents a square area of tissue that is about (0.96) "one micron" high by (0.96) "one micron" wide in size.

At this magnification level, the user receives a higher resolution view of tissue within the lesion 330 itself. As shown here, almost the entirety of the UIDW 310 is now viewing tissue that is inside of the lesion 330. However, a southeast corner of the UIDW 310 straddles an edge of the lesion 330 and displays some tissue that is external to the lesion 330.

This resolution is referred to as a "cellular resolution" or as a "cellular magnification" of the view of the image tissue, because resolution falls within a range of resolution where human cells can be viewed via the UIDW 310. The average size of a human cell is about 100 microns in diameter. At this resolution, a human cell of a size being 100 microns in diameter, such a diameter would be represented by about UIDW 100 contiguous pixels in length, which could occupy about one contiguous inch in size within the 10 inch by 10 inch UIDW 310.

Figure 3F:
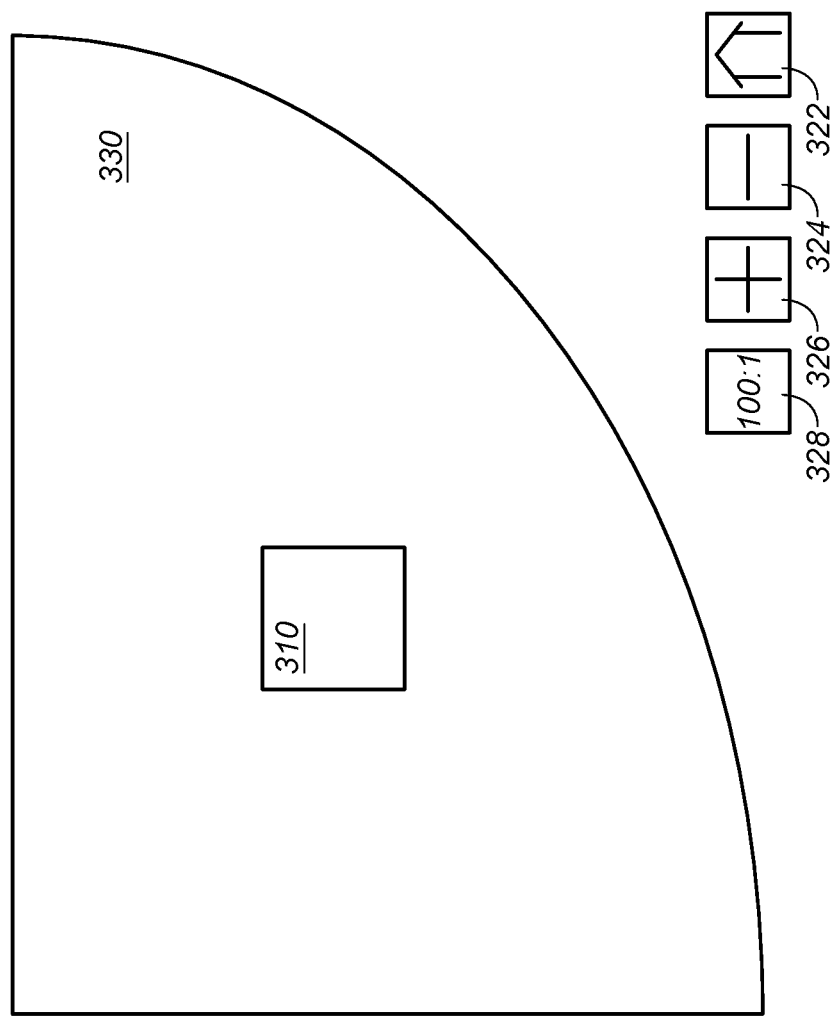
FIG. 3F illustrates updated content of the viewing window in response to a magnification (reduction) directive of FIG. 3F.

FIG. 3F illustrates processing of a fourth viewing directive that is communicated from the user to the IVS 150. This fourth viewing directive causes modification to the view of the image data that is displayed within the UIDW 310, in response to processing the fourth viewing directive. In this scenario, the user now desires a higher magnification (higher resolution) view of the image data in the UIDW 310 than the view of image data being displayed within FIG. 3E.

To again increase magnification of image data being viewed inside of the UIDW 310, the button labeled "+"326, also referred to as the "UP" magnification button 326, is pressed by the user. In response, the content of the UIDW 310 is modified to show a magnified portion of the image data being viewed and having a center point that corresponds to a center point 338 of the image data currently being displayed inside of the UIDW 310.

A third pressing of the UP magnification button 326 increases the linear magnification factor of the image data being displayed from (25 to 1) to (100 to 1), which corresponds to the highest magnification factor and resolution of image data 288 of FIG. 2C. This first highest resolution of image data is equal to the original scanning resolution.

This linear magnification factor equal to (100 to 1) means that a portion of tissue cross-section is magnified 100 times along each of its width dimension and its height dimension, while being displayed inside of the UIDW 310.

This linear magnification factor equal to (100 to 1) is equivalent to an area magnification factor of (100×100=10,000), being a two dimensional magnification factor for an amount of area of the tissue cross-section being displayed inside of the UIDW 310.

In other words, the area of tissue that is being viewed through the entire UIDW 310 at this magnification level, also referred to herein as a display field of view, represents an area that is at most, 1/10,000 of the entire size of the 25 mm square tissue cross-section that was scanned. At this magnification level, each pixel within the UIDW 310 represents a square area of tissue that is about (0.24) "one quarter micron" high by (0.24) "one quarter micron" wide in size.

At this magnification level, the user receives the highest resolution provided by the system, and which is equal to the resolution of the original scanning. The entirety of the UIDW 310 is now displaying tissue that is inside of the lesion 330, and displaying tissue at a cellular resolution.

At this resolution, a human cell of a size being 100 microns in diameter, would be represented by about 400 pixels, occupying about 40% of the width and height, of the dimensions of the UIDW 310.

Performance

In this example use scenario, the performance of surgery upon a patient is suspended, while the patient waits on an operating room table and while the surgeon 116 waits for an evaluation of the optically scanned tissue by another health care specialist. In this circumstance, the IVS 150 is located about 20 miles from the location of where the surgery is currently being performed.

A user of the system, such as a pathologist, for example, receives a notification of image data being available for evaluation, via a mobile device, such as a mobile phone text message, for example, which includes a web site (URL) address and unique identifier of an image data set 126, and information associated with the image data including such as a name of the health care facility where the image data was scanned, type of surgery, name of the patient and name of the surgeon 116 associated with the surgery, for example.

In some embodiments, a portion of the information displayed within the text message can be selected (clicked on) as a URL link and viewed directly on the mobile device, which then operates as a IVS 150. In some embodiments, the notification can also be communicated via electronic mail and viewed directly from a device receiving the electronic mail, in a same manner as described above for the mobile device.

In response, the user accesses a web site by engaging an image viewing station 150 and logs onto a website hosting the Output Image Access Component by authenticating himself or herself with a user name and password, and selects for viewing view the image data set associated with a unique identifier that is listed on the web site. The unique identifier also being supplied by the mobile phone text message via the mobile telephone.

In response to selecting the image data set 126 for viewing, the image viewing station (IVS) 150, being a desktop computer, for example, displays a macro image for this image data set 126, like that shown in FIG. 3A. The elapsed time between the time the user selects an image data set 126 for viewing and the IVS displaying the image data on a display screen, is dependent upon an amount of current Internet activity, which varies over time. However, with typical Internet activity, the elapsed time should typically fall within 8 seconds.

For example, unless the Internet is atypically slow, the Internet should be able to communicate image data of a rate of at least 2.5 Mbytes per second. The image data for the initial display of the macro-view totals to about 2 Mbytes, plus the information associated with the image data set 126 which amounts to less than 10 kilobytes. Hence, at typical internet speeds, the communication of the initial macro-image data should require about 1 second.

However, the round trip time for sending a request to access the image data set 126, which would be first received by the output image access component (OIAC) executing on the Internet web site, then relayed to the input image access component (Input IAC) executing on the image scanning station (ISS), plus time to for the (Input IAC) to retrieve the image data from a high data rate mass storage device that is typically local to the image scanning station, and then the time required to relay the image data from the Input IAC) through the (Output IAC) somewhere (20) miles away from the image scanning station on the Internet, and onto the image viewing station (IVS) could require 3-4 seconds.

The image data is then displayed within the UIDW 310 along with associated user interface controls on the image viewing station, requiring another 1-2 seconds, as described in FIG. 3A. Hence, the total elapsed time would amount to 5-7 seconds. However, if the Internet is atypically slow, the system might require a few more seconds to communicate the image data to the IVS.

In accordance with the invention, the system is designed to limit a user to wait just a small fraction of a minute, and to often wait no more than 8 seconds, to initially view the image data. Unlike other methods of delivering image data, the system is not designed to require a user to wait one or more hours or even minutes to view the image data.

Referring back to FIGS. 3B-3D, the IVS 150 enables the user to drag a location within a displayed image data to a center location within the UIDW 310 in about one second or less, and press the "UP" magnification button 326.

Referring to FIG. 3E, the pressing of the "UP magnification" button 326 typically causes display (zooming) of the viewed image data at a new and higher resolution to appear almost instantly within the UIDW 310. The same is typically true when causing display (zooming) of the viewed image data to a new and lower resolution. At typical Internet speed, panning an image in an amount requiring one additional user interface display window (UIDW) full of new and un-cached image data will, in this use scenario, typically require communication of less than 2.5 megabytes of image data and typically require no more than about 5-7 seconds of elapsed time to access and display the panned image data.

In accordance with the design of the system, the user can interact with the IVS 150 and the image access system and choose a viewing path through a large amount of image data to evaluate the excised tissue, from a distance of 1 yard or from a distance of well more than 100 miles away from the location of the surgery. A communication pathway between an IVC 152 and an Output IAC 142 in combination with a particular image access pathway of communication for the image data being currently viewed, is referred to herein as a viewing pathway of communication between the IVC 152 and the image data set 126 currently being viewed.

FIG. 4 illustrates an expanded overview of communication of image data involving multiple health care facilities 410a-410z. As shown, multiple health care facilities 410a-410z generate scanned image data from surgical procedures and optionally render at least some of the scanned image data available for remote viewing.

Each health care facility has one or more image scanning stations and its own particular configuration (hierarchy) of image access components. A small health care facility may have only one image scanning station, whereas a larger health care facility may have a dozen or more health care scanning stations, with one or more image transfer stations 170 each executing an Intermediate image access component 172 along an image access pathway of communication between an Output IAC 142 and many Input IACs 122.

A plurality of image viewing components 152a-152z that each respectively execute within image viewing stations 150a-150z and access the scanned image data from various locations. The image viewing stations can be located either inside or outside of the health care facilities 210a-210z. Such scanned image data can be viewed from thousands of miles away from the location from which it is was scanned.

The subject matter that is described herein, which refers to image data, can be applied to any type of data, including data that can encode, in part or in whole, other than image data, providing that such data can be stored at a location and communicated to another location via technology that is capable of storing and communicating large amounts, such as at least a million bytes, of data, in a minute or less. Such technology can include employment of electronic and/or optical technology, for example.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

PARTS LIST 110 first health care facility
112 patient
114 operating table
116 surgeon
120 image scanning station (ISS)
122 Input image access component (Input IAC)
124 data storage device, mass storage device
126 image data or image data set
130 user interface display screen (UIDS)
132 keyboard device
134 mouse (screen pointer) device
140 image access portal (IAP)
142 Output image access component (Output IAC)
150 image viewing station (IVS)
152 image viewing component (IVC)
160 confocal (optical) scanner device
161 platen
162 ex-vivo tissue
170 image transfer station (ITS)
172 Intermediate image access component (Intermediate IAC)
210 second health care facility
212 central processing unit (CPU)
214 physical memory
216 input/output hardware
220 system bus
222 operating system
224 mass storage device
228a operating system
228b device drivers
230 image scanning component (ISC)
232 image processing component (IPC)
240 virtual memory
250 image access request, communication
252 image access request
254 image access request
260 image transfer transaction
262 image transfer transaction
264 image transfer transaction
280 third health care facility
282 fourth (highest) resolution of image data 284 third (highest) resolution of image data
286 second (highest) resolution of image data
288 first (highest) resolution of image data
290 network
292 user interface display screen (UIDS)
310 user interface display window (UIDW)
312a-c X, Y and Z axes.
320 user interface controls
322 resolution reset button
324 DOWN magnification button
326 UP magnification button
328 image resolution status indicator
330 lesion
332 user interface display window (UIDW) location
332a-332b cross-hairs indicating a UIDW location
334 northeasterly direction
336 area of UIDW displaying no image data
338 center point location
410 health care facility

What is claimed is:

1. A system for notifying of an availability for access to, and for providing remote and rapid access to, uniquely identified scanned image data, including:
a set of image access components, including one or more input access components, and including one output image access component; and wherein
each of said set of image access components being implemented as computer software, and being configured for notifying a user of a first image viewing component of a uniquely identified first set of image data becoming available for access, at a first location and at a first point in time; and wherein
said first image viewing component being configured for communicating a request to said set of image access components, for access to said first set of image data, and being configured for receiving at least a portion of said first set of image data; and configured for displaying said at least a portion of said first set of image data to said user of said first image viewing component.

2. The system of claim 1 wherein said set of image access components are configured to establish a first access pathway of communication between said first set of image data and said first image viewing component, in response to said communicating a request for access to said first set of image data from said first viewing component.

3. The system of claim 2 wherein said first set of image data becomes unavailable for access at a second point in time, and in response, said first pathway of communication between said first set of image data and said first image viewing component is terminated.

4. The system of claim 1 wherein said set of image access components are configured to form a hierarchy and wherein said at least one input access component functions as a child in relation to one other image access component, and wherein said output image access component functions as a parent to at least one other image access component, within said hierarchy.

5. The system of claim 1 wherein said set of image access components includes at least one intermediate image access component and wherein said intermediate image access component functions as a child in relation to one other image access component and functions as a parent to at least one other image access component.

6. The system of claim 1 wherein said set of image access components are configured for form a tree type of hierarchy, and wherein said output image access component is a root node of said tree type of hierarchy.

7. The system of claim 1 wherein said first set of image data becomes available at a third point in time and at a second location, and in response, a second pathway of communication is established between said first set of image data and said first image viewing component, upon communication of a request for access to said first set of image data, from said first image viewing component.

8. The system of claim 1 wherein said first image viewing component and a second image viewing component each access said first set of image data concurrently over a period of time.

9. The system of claim 1 wherein said first image viewing component accesses said first set of image data and a second set of image data concurrently over time.

10. The system of claim 1 wherein said event of said first set of image data becoming available for access, is not pre-determined with respect to a time of said event.

11. The system of claim 1 wherein said event of said first set of image data becoming available for access, is not pre-determined with respect to a location of said event.

12. The system of claim 1 wherein said first set of image data including image data of various resolutions, and wherein at least one of said various resolutions being different than and computed from, an original scanning resolution of said first set of image data, and wherein said first image viewing component being configured to display image data of said at least one of said various resolutions.

13. The system of claim 1, wherein each of said image access components is implemented as computer software that is configured for executing upon a computer within a network of computers.

14. The system of claim 1, wherein said notifying a user of a first image viewing component of a uniquely identified first set of image data becoming available for access is implemented as a mobile telephone text message and/or as an electronic mail correspondence that is transmitted to said user.

15. The system of claim 1, wherein said displaying occurs in response to said first image viewing component receiving one or more viewing directives from said user of said first image viewing component.

16. A method for notifying of an availability for access to, and for providing remote and rapid access to, uniquely identified scanned image data, including the steps of:
providing a set of image access components, including one or more input image access components and including one output image access component; and wherein
each of said set of image access components being implemented as computer software, and being configured for notifying a user of a first image viewing component of a uniquely identified first set of image data becoming available for access, at a first location and at a first time, and
providing said first image viewing component that is configured for communicating a request to said set of image access components, for access to said first set of image data, and configured for receiving said at least a portion of said first set of image data, and configured for displaying said at least a portion of said first set of image data to said user of said first image viewing component.

17. The method of claim 16 wherein said image data represents human tissue scanned at a human cellular resolution during performance of surgery.

18. The method of claim 16 wherein said notification of said first set of image data becoming available for access, is communicated to said user of said first image viewing component.

19. The method of claim 16, wherein said first set of image data including image data of various resolutions, and wherein at least one of said various resolutions being different than and computed from, an original scanning resolution of said first set of image data, and wherein said first image viewing component being configured to display image data of said at least one of said various resolutions.

20. The method of claim 16, wherein each of said image access components is implemented as computer software that is configured for executing upon a computer within a network of computers.

21. The method of claim 16, wherein said notifying a user of a first image viewing component of a uniquely identified first set of image data becoming available for access is implemented as a mobile telephone text message and/or as an electronic mail correspondence that is transmitted to said user.

* * * * *